(12) United States Patent
Murphy et al.

(10) Patent No.: US 10,617,390 B2
(45) Date of Patent: Apr. 14, 2020

(54) PORTABLE ULTRASOUND USER INTERFACE AND RESOURCE MANAGEMENT SYSTEMS AND METHODS

(71) Applicant: EDAN INSTRUMENTS, INC., Shenzhen (CN)

(72) Inventors: Sean Murphy, Sunnyvale, CA (US); Larry McCabe, Sunnyvale, CA (US); Richard Henderson, Sunnyvale, CA (US)

(73) Assignee: EDAN INSTRUMENTS, INC., Shenzhen (CN)

( * ) Notice: Subject to any disclaimer, the term of this patent is extended or adjusted under 35 U.S.C. 154(b) by 289 days.

(21) Appl. No.: 14/794,645

(22) Filed: Jul. 8, 2015

(65) Prior Publication Data
US 2016/0007965 A1    Jan. 14, 2016

Related U.S. Application Data

(60) Provisional application No. 62/022,613, filed on Jul. 9, 2014.

(51) Int. Cl.
*G06F 3/0481*   (2013.01)
*A61B 8/00*   (2006.01)
(Continued)

(52) U.S. Cl.
CPC .............. *A61B 8/462* (2013.01); *A61B 8/06* (2013.01); *A61B 8/4427* (2013.01); *A61B 8/467* (2013.01);
(Continued)

(58) Field of Classification Search
CPC .................................................. G06F 3/04817
See application file for complete search history.

(56) References Cited

U.S. PATENT DOCUMENTS 5,161,535 A * 11/1992 Short .................. A61B 8/00
                                                345/173
5,757,616 A *  5/1998 May ................. E05B 73/0082
                                                361/679.41
(Continued)

FOREIGN PATENT DOCUMENTS

WO   WO 2006/111874 A2   10/2006
WO   WO 2013/148730 A2   10/2013

OTHER PUBLICATIONS

International Preliminary Report on Patentability issued in related International Patent Application No. PCT/US2015/039610, dated Jan. 10, 2017.
(Continued)

*Primary Examiner* — William Boddie
*Assistant Examiner* — Andrew B Schnirel
(74) *Attorney, Agent, or Firm* — Brett P. Belden; Nikhil T. Pradhan; Foley & Lardner LLP

(57) ABSTRACT

A portable ultrasound system includes a main screen included in a hinged portion of the portable ultrasound system configured to open and close relative to a main housing of the portable ultrasound system, a touchscreen included on a top surface of the main housing of the portable ultrasound system, and a touchpad included on the top surface of the main housing of the portable ultrasound system. The system further includes a processing circuit configured to perform general computing operations, configured to receive ultrasound imaging data, and configured to provide ultrasound information to at least one of the main screen, the touchscreen, or the touchpad.

19 Claims, 24 Drawing Sheets

(51) Int. Cl.

| | | |
|---|---|---|
| *G01S 7/52* | (2006.01) | |
| *G06F 1/16* | (2006.01) | |
| *G06F 3/0354* | (2013.01) | |
| *A61B 8/06* | (2006.01) | |
| *A61B 8/08* | (2006.01) | |
| *G06F 3/0484* | (2013.01) | |
| *G06F 3/0488* | (2013.01) | |
| *G06F 3/0489* | (2013.01) | |

(52) U.S. Cl.
CPC ............ *A61B 8/52* (2013.01); *G01S 7/52084* (2013.01); *G06F 1/1615* (2013.01); *G06F 1/1684* (2013.01); *G06F 3/03547* (2013.01); *G06F 3/0489* (2013.01); *G06F 3/04817* (2013.01); *G06F 3/04842* (2013.01); *G06F 3/04845* (2013.01); *G06F 3/04883* (2013.01); *A61B 8/468* (2013.01); *A61B 8/54* (2013.01); *G06F 2203/0381* (2013.01)

(56) References Cited

U.S. PATENT DOCUMENTS

| | | | | |
|---|---|---|---|---|
| 5,867,163 | A * | 2/1999 | Kurtenbach | ............... G06F 8/34 715/840 |
| 6,436,040 | B1 * | 8/2002 | Collamore | ............... A61B 8/02 600/437 |
| 6,491,630 | B1 | 12/2002 | Saccardo et al. | |
| 6,540,685 | B1 * | 4/2003 | Rhoads | ................... A61B 8/00 600/459 |
| 8,149,224 | B1 * | 4/2012 | Kuo | ..................... G06F 1/1626 345/156 |
| 2002/0173721 | A1 | 11/2002 | Grunwald et al. | |
| 2004/0152982 | A1 * | 8/2004 | Hwang | ............... G01S 7/52079 600/441 |
| 2004/0179332 | A1 * | 9/2004 | Smith | ...................... A61B 8/00 361/679.41 |
| 2005/0033175 | A1 * | 2/2005 | Lee | ........................ A61B 8/06 600/453 |
| 2008/0055826 | A1 | 3/2008 | Smith et al. | |
| 2008/0119731 | A1 | 5/2008 | Becerra et al. | |
| 2008/0125655 | A1 * | 5/2008 | Song | ........................ A61B 8/00 600/443 |
| 2008/0146922 | A1 * | 6/2008 | Steins | .................... A61B 8/546 600/437 |
| 2008/0163130 | A1 * | 7/2008 | Westerman | ......... G06F 3/04883 715/863 |
| 2010/0260398 | A1 * | 10/2010 | Ma | ......................... A61B 6/469 382/131 |
| 2011/0043434 | A1 * | 2/2011 | Roncalez | ............ G06F 3/04847 345/3.1 |
| 2013/0016103 | A1 * | 1/2013 | Gossweiler, III | .. G06K 9/00261 345/428 |
| 2013/0197364 | A1 | 8/2013 | Han | |
| 2013/0324850 | A1 | 12/2013 | Petruzzelli et al. | |
| 2014/0088428 | A1 | 3/2014 | Eun-Ho et al. | |
| 2014/0098049 | A1 * | 4/2014 | Koch | ...................... G06F 3/016 345/173 |
| 2014/0121524 | A1 | 5/2014 | Chiang et al. | |
| 2014/0267932 | A1 * | 9/2014 | Riddell | ................. H04N 5/4403 348/734 |
| 2014/0350357 | A1 * | 11/2014 | Lee | ...................... A61B 8/4427 600/301 |

OTHER PUBLICATIONS

International Search Report and Written Opinion issued in related International Patent Application No. PCT/US2015/39610, dated Mar. 25, 2016.
Extended Search Report for European Patent Application No. 15 818872, dated Jan. 30, 2018.

* cited by examiner

PORTABLE ULTRASOUND USER INTERFACE AND RESOURCE MANAGEMENT SYSTEMS AND METHODS

CROSS-REFERENCE TO RELATED APPLICATION

This application claims the benefit of U.S. Provisional Application No. 62/022,613, filed Jul. 9, 2014, which is hereby incorporated by reference in its entirety.

BACKGROUND OF THE INVENTION

The present invention relates generally to the field of portable ultrasound devices. Ultrasound devices image a patient by producing and emitting ultrasonic waves with a transducer. The transducer measures returning echoes of these waves to provide data regarding the patient. The data may be analyzed and assembled into an image of the patient using a computing device. Typically, potable ultrasound devices are large systems transported on a cart with limited battery life. Alternatively, some portable ultrasound systems are hand held but still relatively large. The present invention includes features which enhance the portability, usability, and configurability or portable ultrasound system.

SUMMARY OF THE INVENTION

One embodiment relates to a portable ultrasound system which includes a main screen included in a hinged portion of the portable ultrasound system configured to open and close relative to a main housing of the portable ultrasound system, a touchscreen included on a top surface of the main housing of the portable ultrasound system, and a touchpad included on the top surface of the main housing of the portable ultrasound system. The system further includes a processing circuit configured to perform general computing operations, configured to receive ultrasound imaging data, and configured to provide ultrasound information to at least one of the main screen, the touchscreen, or the touchpad.

Another embodiment relates to a portable ultrasound system including a main screen included in a hinged portion of the portable ultrasound system configured to open and close relative to a main housing of the portable ultrasound system, a touchscreen included on a top surface of the main housing of the portable ultrasound system, and a processing circuit. The processing circuit is configured to perform general computing operations and configured to receive ultrasound imaging data, provide ultrasound information to at least one of the main screen or the touchscreen, display an ultrasound imaging user interface on the touchscreen including a plurality of control options or settings for use in ultrasound imaging, and receive touch input from the touchscreen and adjust the ultrasound imaging based on the received touch input.

Another embodiment relates to a portable ultrasound system including a main screen included in a hinged portion of the portable ultrasound system configured to open and close relative to a main housing of the portable ultrasound system, a touchpad included on the top surface of the main housing of the portable ultrasound system and configured to receive touch based inputs and display images, and a processing circuit configured to perform general computing operations and configured to receive ultrasound imaging data. The processing circuit is further configured to provide ultrasound information to at least one of the main screen or the touchpad, and configured to control the display of the images on the touchpad.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF THE PREFERRED EMBODIMENTS

Generally, the invention relates features for a portable ultrasound system. The features enhance the portability, configurability, and functionality of the portable ultrasound system. A portable ultrasound system is typically battery powered. The system may also be powered by mains power when available. The portable ultrasound system may be used for obstetrical and gynecological imaging (e.g., measuring the size of a fetus, checking the position of a fetus, etc.), cardiac imaging (e.g., identifying abnormal heart structures, measuring blood flow, etc.), urological imaging, etc. As portable ultrasound systems may be used in less than ideal conditions (e.g., no ready access to power, no formal work station, etc.), the features described herein help to address the problems associated with such use.

Figure 1:
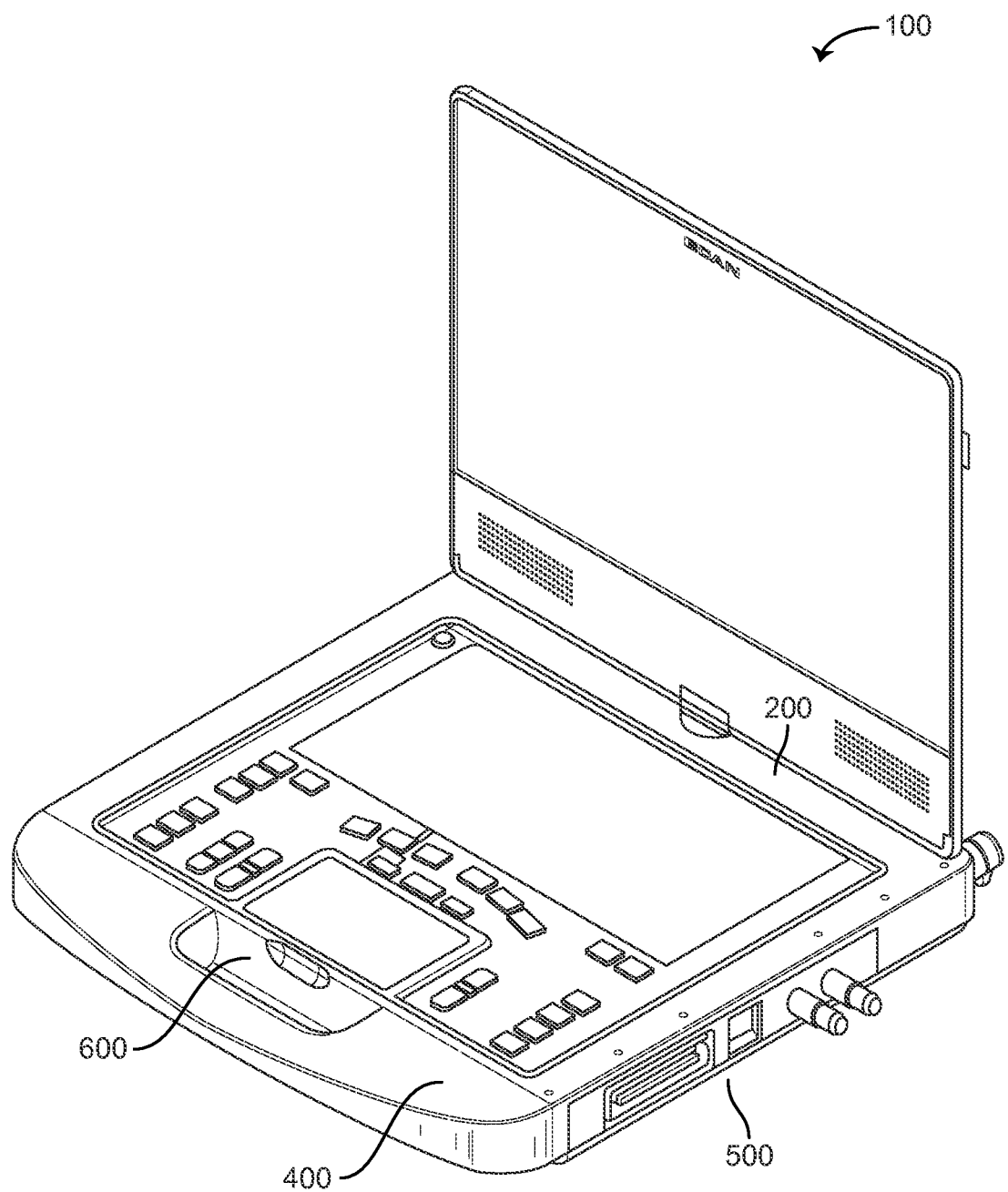
FIG. 1 illustrates an embodiment of a portable ultrasound system incorporating aspects of the invention.

Referring to FIG. 1, one embodiment of portable ultrasound system 100 is illustrated. Portable ultrasound system 100 may include display support system 200 for increasing the durability of the display system. Portable ultrasound system 100 may further include locking lever system 500 for securing ultrasound probes and/or transducers. Some embodiments of portable ultrasound system 100 include ergonomic handle system 400 for increasing portability and usability. Further embodiments include status indicator system 600 which displays, to a user, information relevant to portable ultrasound system 100. Portable ultrasound system 100 may further include features such as an easy to operate and customizable user interface, adjustable feet, a backup battery, modular construction, cooling systems, etc.

Figure 2:
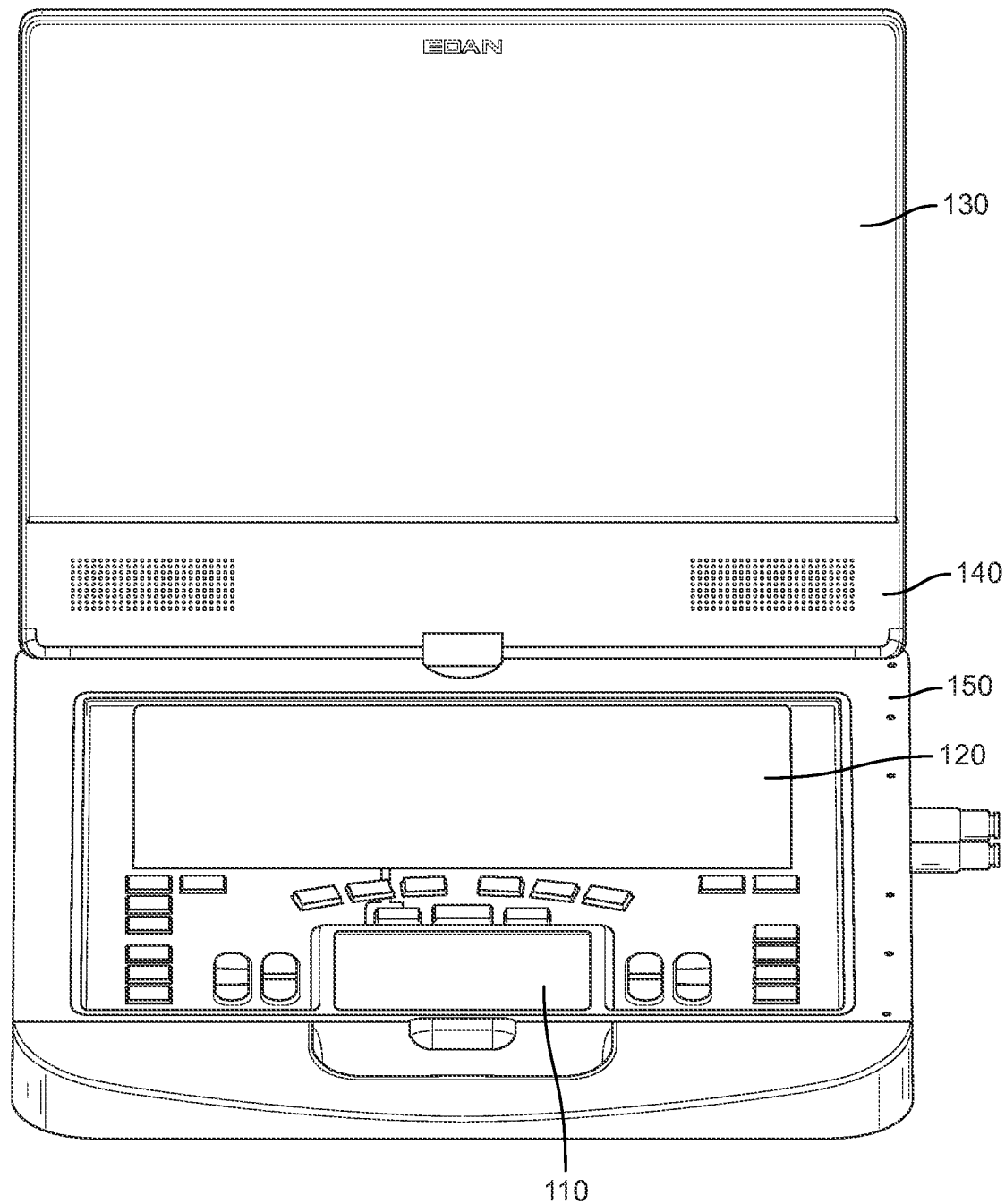
FIG. 2 illustrates a front view of one embodiment of a portable ultrasound system.

Referring to FIG. 2, a front view of one embodiment of portable ultrasound system 100 is illustrated. Main housing 150 houses components of portable ultrasound system 100. In some embodiments, the components housed within main housing 150 include locking lever system 500, ergonomic handle system 400, and status indicator system 600. Main housing 150 may also be configured to support electronics modules which may be replaced and/or upgraded due to the modular construction of portable ultrasound system 100. In some embodiments, portable ultrasound system 100 includes display housing 140. Display housing 140 may include display support system 200. In some embodiments, portable ultrasound system 100 includes touchpad or touchscreen 110 for receiving user inputs and displaying information, touchscreen 120 for receiving user inputs and displaying information, and main screen 130 for displaying information.

Figure 3:
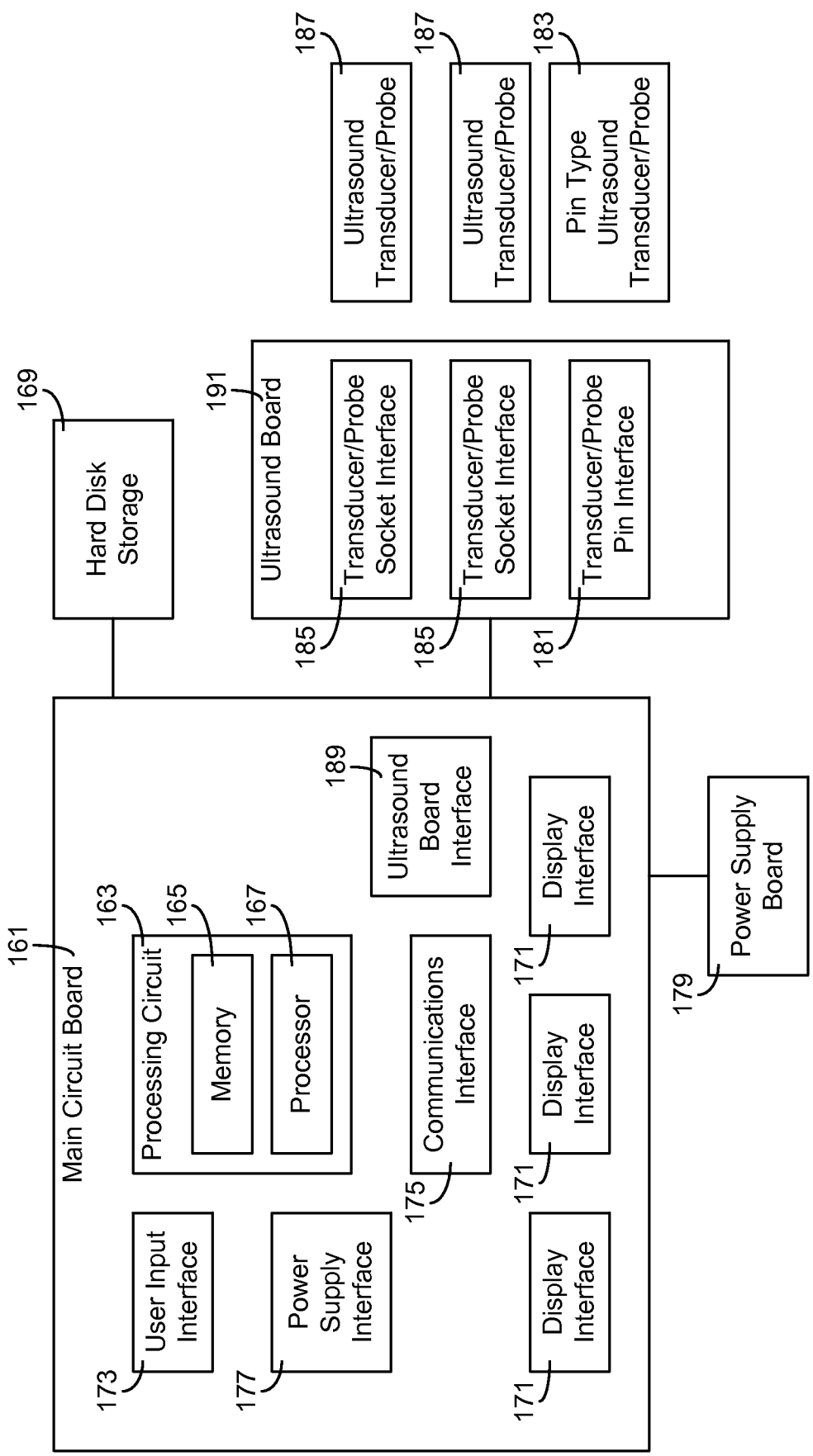
FIG. 3 illustrates a block diagram of components of one embodiment of a portable ultrasound system.

Referring to FIG. 3, a block diagram shows internal components of one embodiment of portable ultrasound system 100. Portable ultrasound system 100 includes main circuit board 161. Main circuit board 161 carries out computing tasks to support the functions of portable ultrasound system 100 and provides connection and communication between various components of portable ultrasound system 100. In some embodiments, main circuit board 161 is configured so as to be a replaceable and/or upgradable module.

To perform computational, control, and/or communication tasks, main circuit board 161 includes processing circuit 163. Processing circuit 163 is configured to perform general processing and to perform processing and computational tasks associated with specific functions of portable ultrasound system 100. For example, processing circuit 163 may perform calculations and/or operations related to producing an image from signals and or data provided by ultrasound equipment, running an operating system for portable ultrasound system 100, receiving user inputs, etc. Processing circuit 163 may include memory 165 and processor 167 for use in processing tasks. For example, processing circuit may perform calculations and/or operations.

Processor 167 may be, or may include, one or more microprocessors, application specific integrated circuits (ASICs), circuits containing one or more processing components, a group of distributed processing components, circuitry for supporting a microprocessor, or other hardware configured for processing. Processor 167 is configured to execute computer code. The computer code may be stored in memory 165 to complete and facilitate the activities described herein with respect to portable ultrasound system 100. In other embodiments, the computer code may be retrieved and provided to processor 167 from hard disk storage 169 or communications interface 175 (e.g., the computer code may be provided from a source external to main circuit board 161).

Memory 165 can be any volatile or non-volatile computer-readable storage medium capable of storing data or computer code relating to the activities described herein. For example, memory 165 may include modules which are computer code modules (e.g., executable code, object code, source code, script code, machine code, etc.) configured for execution by processor 167. Memory 165 may include computer executable code related to functions including ultrasound imagining, battery management, handling user inputs, displaying data, transmitting and receiving data using a wireless communication device, etc. In some embodiments, processing circuit 163 may represent a collection of multiple processing devices (e.g., multiple processors, etc.). In such cases, processor 167 represents the collective processors of the devices and memory 165 represents the collective storage devices of the devices. When executed by processor 167, processing circuit 163 is configured to complete the activities described herein as associated with portable ultrasound system 100.

Hard disk storage 169 may be a part of memory 165 and/or used for non-volatile long term storage in portable ultrasound system 100. Hard disk storage 169 may store local files, temporary files, ultrasound images, patient data, an operating system, executable code, and any other data for supporting the activities of portable ultrasound device 100 described herein. In some embodiments, hard disk storage is embedded on main circuit board 161. In other embodiments, hard disk storage 169 is located remote from main circuit board 161 and coupled thereto to allow for the transfer of data, electrical power, and/or control signals. Hard disk 169 may be an optical drive, magnetic drive, a solid state hard drive, flash memory, etc.

In some embodiments, main circuit board 161 includes communications interface 175. Communications interface 175 may include connections which enable communication between components of main circuit board 161 and communications hardware. For example, communications interface 175 may provide a connection between main circuit board 161 and a network device (e.g., a network card, a wireless transmitter/receiver, etc.). In further embodiments, communications interface 175 may include additional circuitry to support the functionality of attached communications hardware or to facilitate the transfer of data between communications hardware and main circuit board 161. In other embodiments, communications interface 175 may be a system on a chip (SOC) or other integrated system which allows for transmission of data and reception of data. In such a case, communications interface 175 may be coupled directly to main circuit board 161 as either a removable package or embedded package.

Some embodiments of portable ultrasound system 100 include power supply board 179. Power supply board 179 includes components and circuitry for delivering power to components and devices within and/or attached to portable ultrasound system 100. In some embodiments, power supply board 179 includes components for alternating current and direct current conversion, for transforming voltage, for delivering a steady power supply, etc. These components may include transformers, capacitors, modulators, etc. to perform the above functions. In further embodiments, power supply board 179 includes circuitry for determining the available power of a battery power source. In other embodiments, power supply board 179 includes circuitry for switching between power sources. For example, power supply board 179 may draw power from a backup battery while a main battery is switched. In further embodiments, power supply board 179 includes circuitry to operate as an uninterruptable power supply in conjunction with a backup battery. Power supply board 179 also includes a connection to main circuit board 161. This connection may allow power supply board 179 to send and receive information from main circuit board 161. For example, power supply board 179 may send information to main circuit board 161 allowing for the determination of remaining battery power. The connection to main circuit board 161 may also allow main circuit board 161 to send commands to power supply board 179. For example, main circuit board 161 may send a command to power supply board 179 to switch from source of power to another (e.g., to switch to a backup battery while a main battery is switched). In some embodiments, power supply board 179 is configured to be a module. In such cases, power supply board 179 may be configured so as to be a replaceable and/or upgradable module.

Main circuit board 161 may also include power supply interface 177 which facilitates the above described communication between power supply board 179 and main circuit board 161. Power supply interface 177 may include connections which enable communication between components of main circuit board 161 and power supply board 179. In further embodiments, power supply interface 177 includes additional circuitry to support the functionality of power supply board 179. For example, power supply interface 177 may include circuitry to facilitate the calculation of remaining battery power, manage switching between available power sources, etc. In other embodiments, the above described functions of power supply board 179 may be carried out by power supply interface 177. For example, power supply interface 177 may be a SOC or other integrated system. In such a case, power supply interface 177 may be coupled directly to main circuit board 161 as either a removable package or embedded package.

With continued reference to FIG. 3, some embodiments of main circuit board 161 include user input interface 173. User input interface 173 may include connections which enable communication between components of main circuit board 161 and user input device hardware. For example, user input interface 173 may provide a connection between main circuit board 161 and a capacitive touchscreen, resistive touchscreen, mouse, keyboard, buttons, and/or a controller for the proceeding. In one embodiment, user input interface 173 couples controllers for touchpad or touchscreen 110, touchscreen 120, and main screen 130 to main circuit board 161. In other embodiments, user input interface 173 includes controller circuitry for touchpad or touchscreen 110, touchscreen 120, and main screen 130. In some embodiments, main circuit board 161 includes a plurality of user input interfaces 173. For example, each user input interface 173 may be associated with a single input device (e.g., touchpad or touchscreen 110, touchscreen 120, a keyboard, buttons, etc.).

In further embodiments, user input interface 173 may include additional circuitry to support the functionality of attached user input hardware or to facilitate the transfer of data between user input hardware and main circuit board 161. For example, user input interface 173 may include controller circuitry so as to function as a touchscreen controller. User input interface 173 may also include circuitry for controlling haptic feedback devices associated with user input hardware. In other embodiments, user input interface 173 may be a SOC or other integrated system which allows for receiving user inputs or otherwise controlling user input hardware. In such a case, user input interface 173 may be coupled directly to main circuit board 161 as either a removable package or embedded package.

Main circuit board 161 may also include ultrasound board interface 189 which facilitates communication between ultrasound board 179 and main circuit board 161. Ultrasound board interface 189 may include connections which enable communication between components of main circuit board 161 and ultrasound board 191. In further embodiments, ultrasound board interface 189 includes additional circuitry to support the functionality of ultrasound board 191. For example, ultrasound board interface 189 may include circuitry to facilitate the calculation of parameters used in generating an image from ultrasound data provided by ultrasound board 191. In some embodiments, ultrasound board interface 189 is a SOC or other integrated system. In such a case, ultrasound board interface 189 may be coupled directly to main circuit board 161 as either a removable package or embedded package.

In other embodiments, ultrasound board interface 189 includes connections which facilitate use of a modular ultrasound board 191. Ultrasound board 191 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 189 may facilitate replacement of ultrasound board 191 (e.g., to replace ultrasound board 191 with an upgraded board or a board for a different application). For example, ultrasound board interface 189 may include connections which assist in accurately aligning ultrasound board 191 and/or reducing the likelihood of damage to ultrasound board 191 during removal and or attachment (e.g., by reducing the force required to connect and/or remove the board, by assisting, with a mechanical advantage, the connection and/or removal of the board, etc.).

In embodiments of portable ultrasound system 100 including ultrasound board 191, ultrasound board 191 includes components and circuitry for supporting ultrasound imaging functions of portable ultrasound system 100. In some embodiments, ultrasound board 191 includes integrated circuits, processors, and memory. Ultrasound board 191 may also include one or more transducer/probe socket interfaces 185. Transducer/probe socket interface 185 enables ultrasound transducer/probe 187 (e.g., a probe with a socket type connector) to interface with ultrasound board 191. For example, transducer/probe socket interface 185 may include circuitry and/or hardware connecting ultrasound transducer/probe 187 to ultrasound board 191 for the transfer of electrical power and/or data. Transducer/probe socket interface 185 may include hardware which locks ultrasound transducer/probe 187 into place (e.g., a slot which accepts a pin on ultrasound transducer/probe 187 when ultrasound transducer/probe 187 is rotated). In some embodiments, ultrasound board 191 includes two transducer/probe socket interfaces 185 to allow the connection of two socket type ultrasound transducers/probes 187.

In some embodiments, ultrasound board 191 also includes one or more transducer/probe pin interfaces 181. Transducer/probe pin interface 181 enables ultrasound transducer/probe 183 (e.g., a probe with a pin type connector) to interface with ultrasound board 191. Transducer/probe pin interface 181 may include circuitry and/or hardware connecting ultrasound transducer/probe 183 to ultrasound board 191 for the transfer of electrical power and/or data. Transducer/probe pin interface 181 may include hardware which locks ultrasound transducer/probe 183 into place. In some embodiments, ultrasound transducer/probe 183 is locked into place with locking lever system 500. In some embodiments, ultrasound board 191 includes more than one transducer/probe pin interfaces 181 to allow the connection of two or more pin type ultrasound transducers/probes 183. In such cases, portable ultrasound system 100 may include one or more locking lever systems 500. In further embodiments, ultrasound board 191 may include interfaces for additional types of transducer/probe connections.

With continued reference to FIG. 3, some embodiments of main circuit board 161 include display interface 171. Display interface 171 may include connections which enable communication between components of main circuit board 161 and display device hardware. For example, display interface 171 may provide a connection between main circuit board 161 and a liquid crystal display, a plasma display, a cathode ray tube display, a light emitting diode display, and/or a display controller or graphics processing unit for the proceeding or other types of display hardware. In some embodiments, the connection of display hardware to main circuit board 161 by display interface 171 allows a processor or dedicated graphics processing unit on main circuit board 161 to control and/or send data to display hardware. Display interface 171 may be configured to send display data to display device hardware in order to produce an image. In some embodiments, main circuit board 161 includes multiple display interfaces 171 for multiple display devices (e.g., three display interfaces 171 connect three displays to main circuit board 161). In other embodiments, one display interface 171 may connect and/or support multiple displays. In one embodiment, three display interfaces 171 couple touchpad or touchscreen 110, touchscreen 120, and main screen 130 to main circuit board 161.

In further embodiments, display interface 171 may include additional circuitry to support the functionality of attached display hardware or to facilitate the transfer of data between display hardware and main circuit board 161. For example, display interface 171 may include controller circuitry, a graphics processing unit, video display controller, etc. In some embodiments, display interface 171 may be a SOC or other integrated system which allows for displaying images with display hardware or otherwise controlling display hardware. Display interface 171 may be coupled directly to main circuit board 161 as either a removable package or embedded package. Processing circuit 163 in conjunction with one or more display interfaces 171 may display images on one or more of touchpad or touchscreen 110, touchscreen 120, and main screen 130.

Generally, a logic circuit or logic circuitry handles user inputs through the user interface of portable ultrasound system 100. The logic circuit processes user inputs and responds to user inputs. This may include controlling hardware components such as displays, networking devices, ultrasound transducers, etc. Additionally, the logic circuit may respond to user inputs by taking an action through a software component of portable ultrasound system 100. For example, the logic circuit may alter the priority of a hardware device for purposes of allocating physical resources such as processing recourses, memory, input devices, output devices, etc.

With reference to FIG. 3, the logic circuit controls portable ultrasound system 100. The logic circuit may control portable ultrasound system 100 through a combination of programming, default states, user inputs, event response, outputs, etc. In some embodiments, the logic circuit is incorporated into main circuit board 161. For example, the logic circuit may be implemented as processing circuit 163. Alternatively, processing circuit 163 may perform the functions of the logic circuit set above including acquiring user inputs, processing user inputs, and controlling hardware. In some embodiments, processing circuit 163 makes use of other resources included within main board 161 in controlling portable ultrasound system 100. For example, processing circuit 163 may receive user inputs through user input interface 173 and control hardware through display interface 171, communications interface 175, ultrasound board interface 189, ultrasound board 191, and/or user input interface 173. In some embodiments, user inputs and display outputs occur through an operating system and/or graphical user interface (GUI). Computer code and/or instructions for implementing the operating system and/or GUI through event handling, input handling, hardware control, etc. may be stored in memory 165. In further embodiments, computer code and/or instructions regarding the above may be stored in hard disk storage 169 and/or acquired or received by processing circuit 163 using communications interface 175 and a communications device. The operating system and/or GUI may be implemented across one or more of main screen 130, touchscreen 120, and touchpad or touchscreen 110.

Figure 4A:
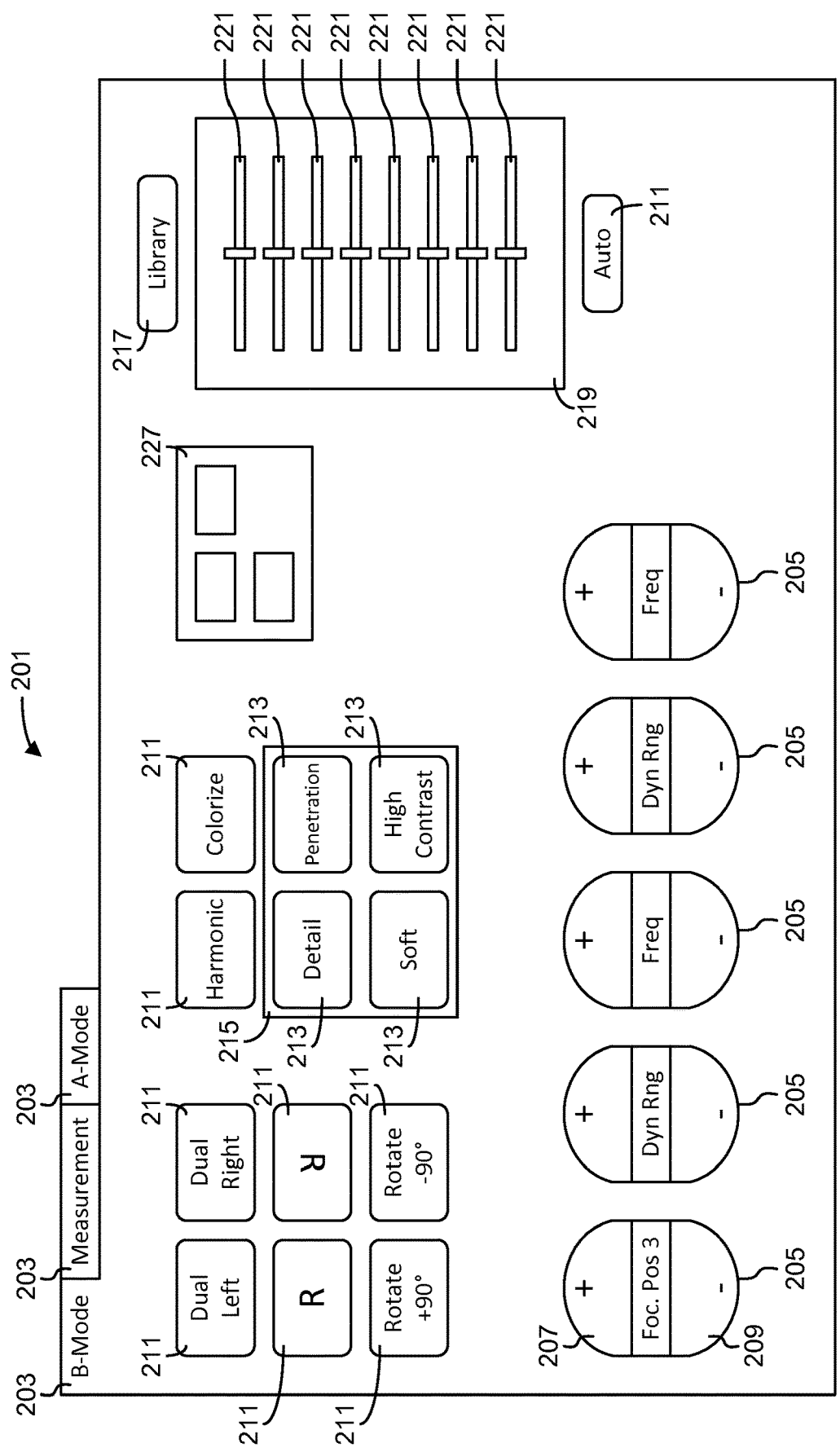
FIG. 4A illustrates an embodiment of a touchscreen user interface having a configurable interface for accepting user inputs and/or displaying information to a user.

FIG. 4A illustrates an embodiment of touchscreen user interface ("touchscreen UI") 201 having a configurable interface for accepting user inputs and/or displaying information to a user. In some embodiments, touchscreen UI 201 is implemented on touchscreen 120. Touchscreen 120 allows for display of buttons, sliders, and other input schemes associated with touchscreen UI 201. Touchscreen 120 also allows for information to be displayed to the user regarding values associated with functions, active functions, visual feedback that a control has been activated, etc. In other embodiments, touchscreen UI 201 is implemented on other input devices. For example, touchscreen UI 201 may be implemented on touchpad or touchscreen 110. In other embodiments, main screen 130 is a touchscreen and touchscreen UI 201 is implemented on main screen 130.

In some embodiments, touchscreen UI 201 includes tabs 203. Each tab 203 corresponds to a particular function of portable ultrasound system 100. For example, these functions may include B-mode imaging for imaging a patient using brightness modulation, measurement for taking measurements of imaged features, A-mode for amplitude modulation imaging, etc. The function which owns touchscreen 120 as an input device (e.g., the currently selected function tab) is signified by the corresponding tab forming a part of the screen containing available settings, buttons, fields, information, etc. Functions which are not currently selected but are active (e.g., the functions which may receive inputs from input devices other than the ones owned by the selected function) are signified by the corresponding tab being displayed as a selectable choice but not an integral part of the screen containing input widgets or controls. Each active function claims touchscreen 120 as a resource, but only the selected function owns the resource so as to receive inputs from the controls or widgets. Input devices and/or resources which are not owned by a function may be owned by other functions according to their priority assigned by processing circuit 163.

A user may switch between functions by selecting a function using its corresponding tab 203. Pressing touchscreen 120 over tab 203 selects tab 203. The function associated with the selected tab then owns the resource of touchscreen 120. A plurality of tabs 203 may be used to manage multiple functions. In some embodiments, up to six tabs 203 are used to manage up to six active (e.g., running) functions. In other embodiments, there is no limit to the number of tabs 203 that a user may create by running a function. A user may be prompted by portable ultrasound system 100 through touchscreen UI 201, touchpad or touchscreen 110, and/or main screen 130 to close functions which have not been recently used. Closing or exiting functions may free up resources (e.g., computational resources, input devices, output devices, etc.) for the remaining active functions. In some embodiments, the prompt may be voluntary. In other embodiments, the prompt may force a user to close a function before a user may continue. In further embodiments, two to three open tabs 203 are common. In alternative embodiments, some functions may run or otherwise be active without being displayed with an associated tab 203. Tabs 203 may be replaced with other navigational alternatives. For example, functions may associated with windows. The windows may be minimized, maximized, exited, switched between, etc. In other embodiments, tabs 203 may be replaced with icons corresponding to each active function. Selecting (e.g., pressing) an icon way select the function associated with the icon. In some embodiments the icons remain visible in a ribbon displayed on touchscreen 120 through touchscreen UI 201. In other embodiments, tabs 203, icons, or other identifiers associated with active functions are normally hidden. The identifiers may become visible following a user gesture. For example, swiping a finger in from an edge may display the identifiers allowing a user to select a function.

When a function is selected, in some embodiments using tab 203, the widgets associated with that function are displayed on touchscreen 120. Using widgets, a user may interact with portable ultrasound system 100. Some embodiments of touchscreen UI 201 include continuous controls 205, radio buttons 213, buttons 211, tabs 203, and/or sliders 221 as widgets. In further embodiments, touchscreen UI 201 may also include widgets such as windows, text boxes, hyperlinks, drop-down lists, list boxes, combo boxes, check boxes, cycle buttons, datagrids, etc.

Continuous controls 205 may be used for adjusting parameters having a plurality of selectable values. In some embodiments, continuous controls 205 are used for adjusting parameters having a wide range of values. Pressing on the bottom 209 of continuous control 205 decreases the value of the parameter controlled by continuous control 205 by one increment. Pressing on the top 207 of continuous control 205 increases the value of the parameter controlled by continuous control 205 by one increment. In some embodiments, continuous control 205 may also be controlled by a user pressing a portion of continuous control 205 and dragging. Pressing continuous control 205 and dragging up or down vertically causes a continuous change in the value of the parameter controlled by continuous control 205. For example, pressing continuous control 205 and dragging upward causes the value of the parameter to continuously increase. Pressing continuous control 205 and dragging downward causes the value of the parameter to continuously decrease. In some embodiments, the continuous change of the value stops when a user removes their finger from touch screen 205. In other embodiments, the continuous change of the value stops when a user drags their finger off of the area defined by the graphic of continuous control 205. In alternative embodiments, the continuous change may continue as long as a user's finger remains on touchscreen 120. In further embodiments, multiple of the above described control schemes may apply. For example, the continuous change may stop if the user either removers their finger from touchscreen 120 or drags their finger outside of the region defined by the graphic of continuous control 205.

In some embodiments, touchscreen UI 201 is programmed and implemented by main processing circuit 163 such that some non-vertical motion while using continuous control 205 is tolerated. This may allow a user to provide inputs through continuous control 205 which include some horizontal movement and/or dragging of the user's finger. For example, processing circuit 163 may determine if a user's input was intended to be a vertical drag by looking at the initial angle of movement. If the angle is sufficiently vertical, processing circuit 163 may read the input as a vertical drag and adjust the parameters associated with continuous control 205 accordingly. The angle may be calculated using two or more input points along the movement of the user's finger registered by touchscreen 120. These points may be taken closely following the user pressing touchscreen 120. In other embodiments, the points may include points registered just before a user removes their finger from touchscreen 120. In further embodiments, other or additional techniques may be used to tolerate some non-vertical movement associated with a user input through continuous control 205.

In some embodiments, space near the bottom of touchscreen UI 201 is reserved for continuous control 205 widgets. For example, five continuous control widgets may be located along the bottom of touchscreen UI 201. In some embodiments, continuous control widgets 205 are the only widgets that may be placed near the bottom of touchscreen UI 201. User attempts at customization including placing non continuous control 205 widgets in this area may be prevented. In additional embodiments, continuous control widgets 205 may not be placed in other locations. A user attempt to do so by customizing touchscreen UI 201 may be prevented by the programming of touchscreen UI 201. In further embodiments, continuous controls 205 may be placed within touchscreen UI 201 such that a continuous control 205 associated with a particular parameter is placed above a physical control (e.g., knob, wheel, slider, buttons, etc.) which also control the same parameter. In alternative embodiments, the non-customizable location of continuous controls 205 may be in other areas of touchscreen UI 201. For example, continuous controls 205 may be located along the top of touchscreen UI 201 or along one or more sides of touchscreen UI 201. In further embodiments, the location of continuous controls 205 is customizable by a user.

In some embodiments, continuous controls 205 display a range of possible values for the parameter controlled by the continuous control 205. Continuous control 205 may also display the current value of the parameter. For example, the current value may be displayed next to the label on continuous control 205 identifying the parameter that is controlled. The maximum value at which the parameter may be set may be displayed above the label identifying the parameter that is controlled. The minimum value at which the parameter may be set may be displayed below the label identifying the parameter that is controlled. In other embodiments, the current parameter value, minimum parameter value, and/or maximum parameter value may be displayed in other locations. For example, the value may be displayed along a number line below, above, to the side of, or on continuous control 205. The maximum value may be displayed in the top 207 of continuous control 205, the minimum value may be displayed in the bottom 209 of continuous control 205, and the current value may be displayed next to the label identifying continuous control 205.

Buttons 211 may be used for parameters which generate an event or have two states (e.g., on or off). For example, a button 211 may generate an event by rotating an image when pressed by a user. Continuing the example, a button 211 may have two states such as a button which when pressed colorizes and image and when pressed again reverts the image to grayscale/black and white. In some embodiments, buttons 211 have an off state and an on state. Pressing the button 211 widget toggles the state. Touchscreen UI 201 may display a different image for a button 211 depending on the current state of the button. A button 211 in a first state may be displayed with a background of a first color and a background of a second color when the button 211 is in a second state. Alternatively or additionally, a button 211 in a first state may be displayed with label font of a first color and with label font of a second color when the button 211 is in a second state. Alternatively or additionally, a button 211 may have a different label when in different states. For example, a button 211 may be labeled "colorize" while an image is displayed in grayscale. Pressing the button 211 may colorize the image and result in the button being labeled "grayscale." Pressing the button 211 may revert the image to a grayscale image and the button 211 would again be labeled "colorize." Each of the two states of button 211 may be distinguished from each other.

In other embodiments, some buttons 211 may generate an event each time the button 211 is pressed. For example, a button 211 may rotate an image ninety degrees clockwise each time the button 211 is pressed. For example, pressing a button 211 once may rotate an image ninety degrees from its first position. Pressing the button 211 for a second time may rotate the image to a position 180 degrees from its first position, and pressing the button 211 for a third time may rotate the image 270 degrees from its first position. In some embodiments, each time button 211 is pressed touchscreen UI 201 indicates that a user input has been received. This indication to a user may be provided by changing a characteristic of a button temporarily. For example, the color of the background of the button 211 and/or of the label text may change temporarily. In other embodiments, a characteristic of button 211 may remain changed until the button 211 is pressed again.

With continued reference to FIG. 4A, some embodiments of touchscreen UI 201 include radio buttons 213. Radio buttons 213 allow user input from a selected group of options with only one input being possible at a single time. When one radio button 213 is activated, the others in the same group of radio buttons may not be selected without deselecting or deactivating the previous radio button. In some embodiments, selecting a radio button 213 from a group of linked radio buttons 213 automatically deselects or deactivates the previous radio button 213. Upon startup of touchscreen UI 201, one radio button 213 of each group of radio buttons may be selected or active by default. In other embodiments, a user must deselect a radio button 213 to select or activate a radio button 213 in the same group.

In some embodiments, touchscreen UI 201 allows for customization regarding the location of widgets. In embodiments allowing a user to position radio buttons 213, touchscreen UI 201 and radio buttons 213 may be configured to show the relationship between radio buttons 213 in a single group. For example, radio buttons 213 may be placed individually anywhere on the home screen of touchscreen UI 201. When radio buttons 213 from a single group are placed next to each other, the relationship between the radio buttons (e.g., that they are connected and only one may be selected at a time) is indicated by a radio button graphic 215 which surrounds the radio buttons 213 of the group. When two or more groups of radio buttons 213 are included in touchscreen UI 201, multiple radio button graphics 215 may be used to signify the relations of the radio buttons. In some embodiments, the color, pattern, image, etc. of each radio button graphic 215 may be different in order to differentiate groups of related radio buttons 213.

In some embodiments, a user may locate radio buttons 213 such that they are not placed next to each other. In such a case, radio buttons 213 may have characteristics to illustrate to the user which radio buttons 213 form a group. For example, all radio buttons 213 of a single group may be colored identically. A first group of radio buttons 213 may have green backgrounds while a second group of radio buttons 213 may have blue backgrounds. In other embodiments, the relationship between radio buttons 213 of a single group may be signified by each radio button 213 of a group having the same shape, text color, text font, size, etc. The radio buttons 213 of a second group having a differentiating feature in of the same type.

In some embodiments, touchscreen UI 201 further includes a button which when pressed invokes a sub-screen with additional controls. The additional controls may be activated from the sub-screen. In some embodiments, the additional controls may be added to the screen associated with a function tab 203 through touchscreen UI 201 customization inputs. In one embodiment, a library button 217 is included in touchscreen UI 201 for accessing additional controls not found on the screen associated with a tab 203 for a function. In some embodiments, library button 217 includes controls and/or widgets for all available functions. In other embodiments, library button 217 includes controls and/or widgets available only for the selected function (e.g., the function associated with the tab 203 selected by the user and the screen on which the library button 217 is displayed).

Figure 5A:
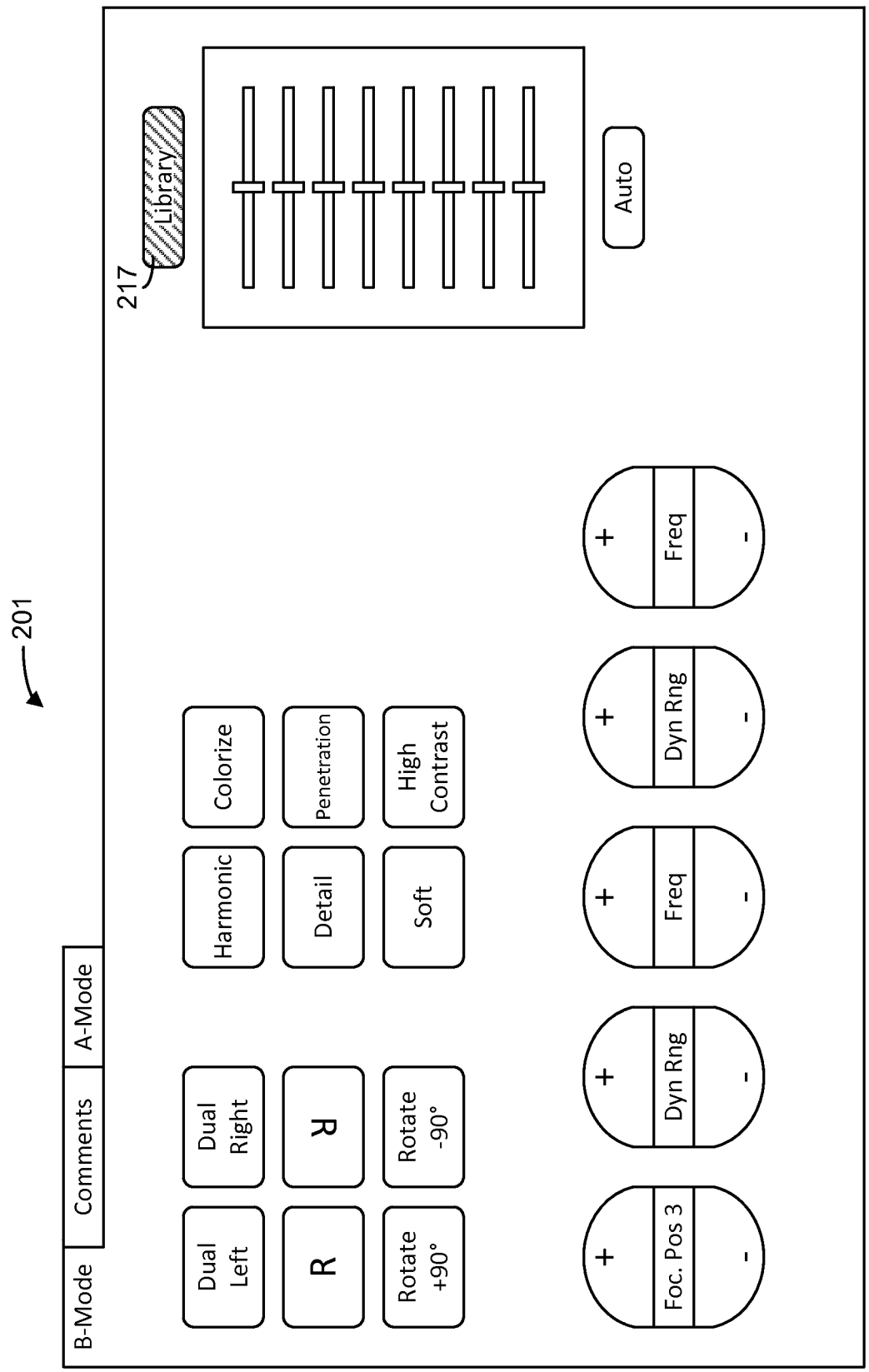
FIG. 5A illustrates a library button of a user interface according to an exemplary embodiment.

Referring now to FIG. 5A, touchscreen UI 201 is depicted with a user pressing library button 217. This is illustrated with the hatching on library button 217. Pressing library button 217 provides a user access to the additional controls referenced above.

Figure 5B:
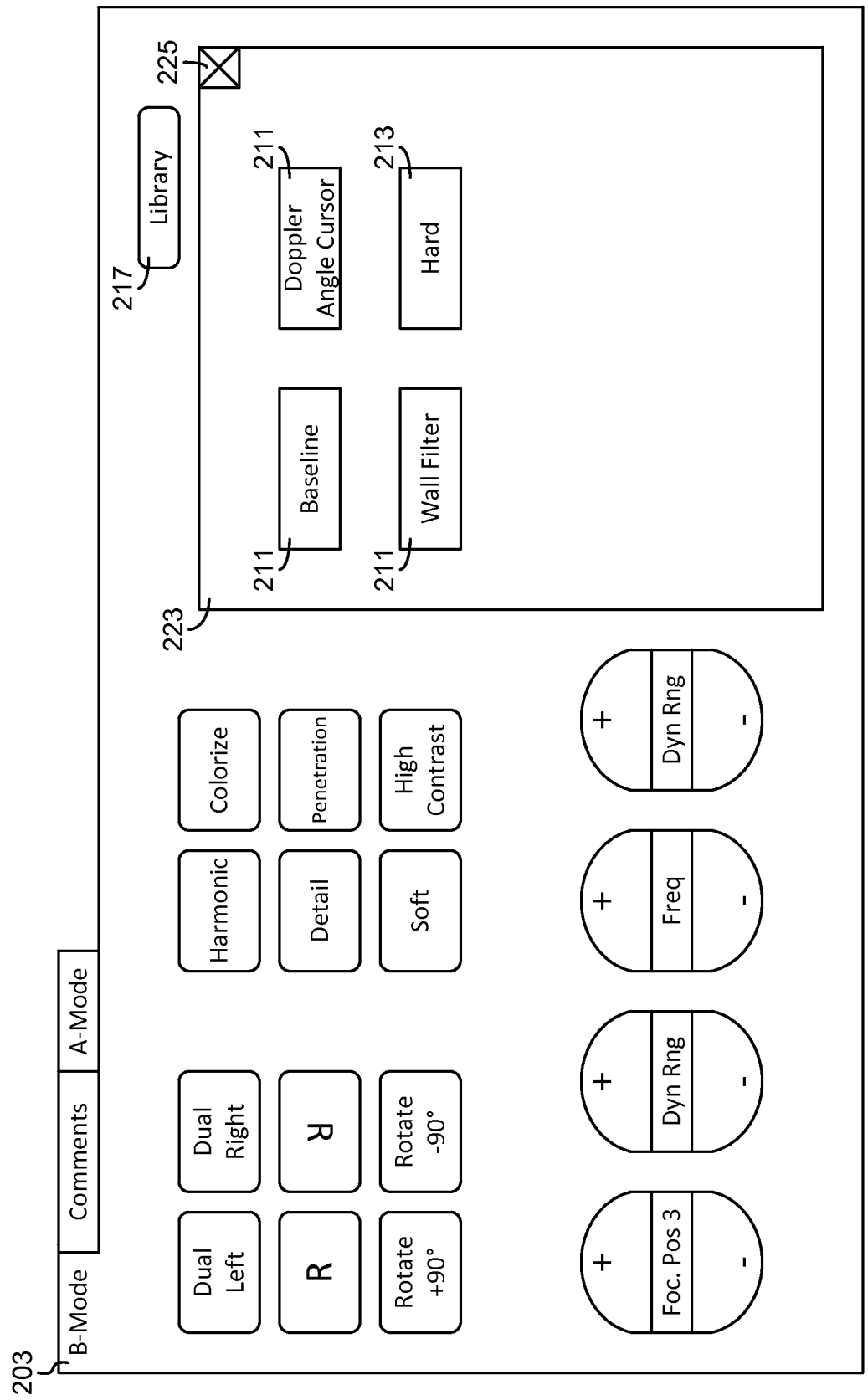
FIG. 5B illustrates a user interface following the selection of a library button according to an exemplary embodiment.

Referring now to FIG. 5B, touchscreen UI 201 is depicted following a user pressing library button 217. In response to a user pressing library button 217, sub-screen 223 is displayed in touchscreen UI 201. In some embodiments, sub-screen 201 is a window displayed over all or a portion of the display associated with tab 203 and the currently selected function. This may be displayed on touchscreen 120. In alternative embodiments, sub-screen 223 may be displayed as an additional tab 203 which a user can access by pressing the tab 203. In other embodiments, sub-screen 201 may be displayed and interacted with on other input/display devices such as touchpad or touchscreen 110 or main screen 130. In one embodiment, sub-screen 223 is a window which overlays the screen associated with the currently selected tab 203. Sub-screen 223 covers some widgets but leaves library button 217 unobscured.

Sub-screen 223 includes additional widgets. Sub-screen 223 may include widgets such as buttons 211 and/or radio buttons 213. In some embodiments, sub-screen 223 may further include continuous controls 205, sliders 221, text boxes, hyperlinks, drop-down lists, list boxes, combo boxes, check boxes, cycle buttons, datagrids, etc. A user may provide an input by pressing a widget or otherwise controlling the widget through sub-screen 223. In some embodiments, a user may also customize the screen associated with a particular function and tab 203 by adding widgets from sub-screen 203 or removing widgets from the screen and adding them to sub-screen 203.

In some embodiments, a user has the option of moving sub-screen 223 to various positions on the screen. Sub-screen 223 may be moved by pressing and holding sub-screen 223 and dragging sub-screen 223 to the desired position. In some embodiments, a user may press and hold anywhere on sub-screen 223. In other embodiments, a user must press and hold a portion of sub-screen 223 that is not overlaid by a widget. In further embodiments, sub-screen 223 may include a header section which a user may press and hold while dragging to position sub-screen 223.

In additional embodiments, a user is able to resize sub-screen 223. A user may resize sub-screen 223 by pinching or expanding with two fingers pressing a portion of sub-screen 223. In other embodiments, one or more buttons are provided to allow a user to select from pre-determined sizes of sub-screen 223 or to resize sub-screen 223 to a custom size. In some embodiments, sub-screen 223 may include one or more scroll bars which allow a user to access additional widgets. A user may navigate through sub-screen 223 by pressing on the scroll bar. In other embodiments, a user may navigate through sub-screen 223 by swiping a finger in the direction the user wants to scroll. In further embodiments, sub-screen 223 includes pages of widgets. Each page may be organized according to a common scheme. For example, widgets may be organized alphabetically, according to frequency of use, by category of control, by type of widget (e.g., buttons, radio buttons, sliders, etc.), etc. In some embodiments, pages may be viewed by swiping a finger. In other embodiments, pages may be designated with corresponding tabs 203. Tabs 203 within sub-screen 223 may be labeled with category names identifying the widgets on the corresponding page.

In one embodiment, a user exits sub-screen 223 and return to the screen by pressing close button 225. In some embodiments, a user exits sub-screen 223 by pressing library button 217 while sub-screen 223 is displayed. In other embodiments, a user exits sub-screen 223 by pressing anywhere outside of sub-screen 223 (e.g., pressing a portion of the screen not overlaid by sub-screen 223). In further embodiments, a user is returned to the screen and sub-screen 223 is closed once a user presses a widget or otherwise uses a control in sub-screen 223. In alternative embodiments, one or more of the above exit configurations may be used in combination with other exit configurations.

Referring again to FIG. 4A, some embodiments of touchscreen UI 201 include sliders 221. Sliders may be used to adjust parameters or otherwise provide inputs through touchscreen UI 201. A user may press and hold slider 221 and drag the slider until the desired setting is reached. A user may then stop pressing slider 221 in order to set the parameter at the desired value. In some embodiments, a user may also press anywhere along slider 221 in order to set the parameter at that value.

Some embodiments of touchscreen UI 201 include distance gain compensation or depth gain compensation widget ("DGC widget") 219. DGC widget 219 is used to adjust the gain. Amplification may be adjusted with DGC widget 219 while imaging a patient. DGC widget 219 may allow for the gain to be adjusted at various positions of the imaged area. The gain may be altered for various sections of the image. In some embodiments, DGC widget 219 includes a plurality of sliders 221 for adjusting gain at various locations. For example, sliders 221 positioned at the top of the widget may correspond to gain adjustments to the area imaged near the top of the image displayed on main screen 130. Similarly sliders 221 positioned at the bottom of DGC widget 219 correspond to gain adjustment to the area imaged near the bottom of the image displayed on main screen 130.

Pressing and dragging one of the sliders 221 horizontally will change the gain corresponding to the individual slider 221. For example, the gain may be increased when the slider 221 is dragged to the right. The gain may be reduced when the slider 221 is dragged to the left. In some embodiments, swiping vertically on DGC widget 219 will move each slider 221 in an amount proportional to the horizontal distance between the finger and slider 221 as the finger passes that slider 221. In other embodiments, swiping vertically along DGC widget 219 will move each slider 221 to the position at which the finger swipes through that slider 221.

Figure 4B:
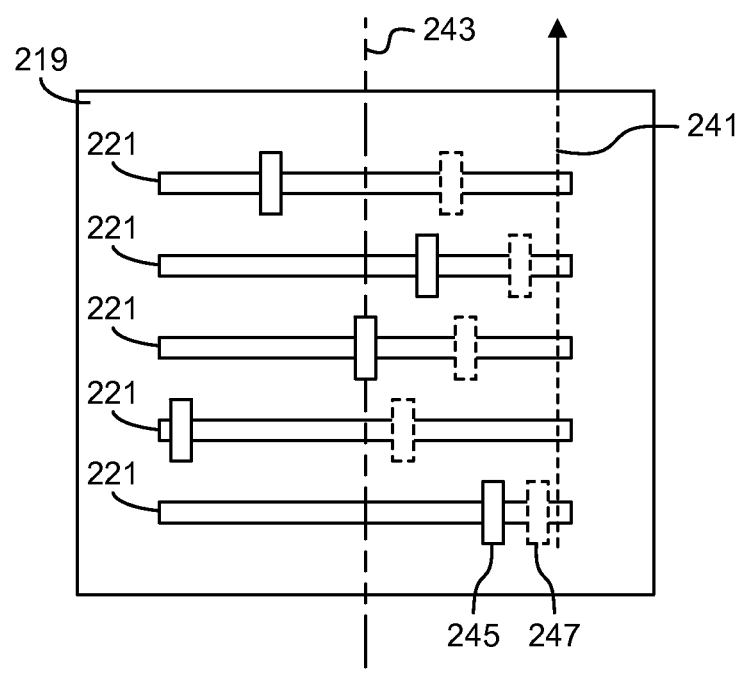
FIG. 4B illustrates an embodiment of a depth gain compensation widget.

With reference to FIG. 4B, an embodiment of DGC widget 219 is illustrated operating according to vertical swipe described above. Dashed line 241 illustrates a vertical finger swipe up through sliders 221. Center line 243 indicates the center of DGC widget 219. The first position 245 of each slider 221 prior to the vertical finger swipe 241 is indicated by the solid sliders. The second position 247 of each slider 221 after the vertical finger swipe 241 is indicated by the dashed slider.

Following a vertical finger swipe 241 sliders 221 are adjusted according to the distance between the first position 245 and the line created by the finger swipe 241. In some embodiments, the slider 221 is adjusted from first position 245 to second position 247 proportionally to the distance between the first position 245 and the finger swipe 241. Thus, the greater the distance between first position 245 and finger swipe 241, the greater the value by which slider 221 is adjusted to second position 247. Each slider 221 may be adjusted by a different amount depending on its first position 245 relative to the finger swipe 241. In other embodiments, slider 221 may be adjusted by a different amount. For example, a vertical swipe 241 may move all sliders 221 a set amount, the value by which each slider 221 is adjusted may be calculated based on an average location of all sliders 221, etc.

In some embodiments, the direction in which the sliders 221 are adjusted (e.g., gain is increased or decreased) is determined based on which side of center line 243 the finger swipe 241 occurs. In some embodiments, swiping vertically on the right side of center line 243 increases the gain of sliders 221. In one embodiment, if the first position 245 of a slider 247 is at a higher gain than a vertical finger swipe 241 which increases gain, the slider 221 is not adjusted. In another embodiment, the slider 221 is increased by the proportional distance from the finger swipe 241. Vertical finger swipes 241 which reduce gain may function in the same manner. In other embodiments, sliders 221 are proportionally increased or decreased based on which side of vertical finger swipe 241 the first position 245 falls. A singe vertical finger swipe 241 may cause an increase in gain in some sliders 221 while also causing a decrease in gain in other sliders 221. Advantageously, a user can adjust multiple gain settings of DGC widget 219 with a single gesture. This increases the efficiency of setting the appropriate values of DGC widget 219 and increases the ease of use of the DGC widget 219.

In some embodiments, DGC widget 219 may include labels for each slider 221 which indicate the current gain setting for each slider 221. Some embodiments of DGC widget 219 also include a button which returns each slider 221 to a default position. Further embodiments of DGC widget 219 include an auto button which sets each slider 221 according to an algorithm for optimizing the gain. Some embodiments of touchscreen UI 201 may also include a widget similar to the DGC widget 219 for adjusting gain such as a time gain compensation widget.

Generally, some embodiments of touchscreen UI 201 include one-shot widgets. Pressing a one-shot widget generates an event. While the widget is pressed, the appearance of the widget changes to indicate that the widget has been pressed. In some embodiments, the appearance of the widget remains changed for the duration of the event. Once the one-shot widget is released, the widget returns to its original appearance. In other embodiments, the widget returns to its original appearance after the duration of the event. In some embodiments of touchscreen UI 201, various types of widgets may be one-shot widgets.

Referring now to FIG. 4A, some embodiments of touchscreen UI 201 include folders 227 which store multiple widgets in a single group. In some embodiments, pressing on the folder 227 widget displays the content of the folder 227 (e.g, the folder 227 is opened). In other embodiments, the contents of folder 227 are accessed using other or additional gestures. The gestures may be any of the gestures described herein (e.g., swipe, multiple-finger press, press and hold, multiple-finger swipe, etc.).

Figure 4C:
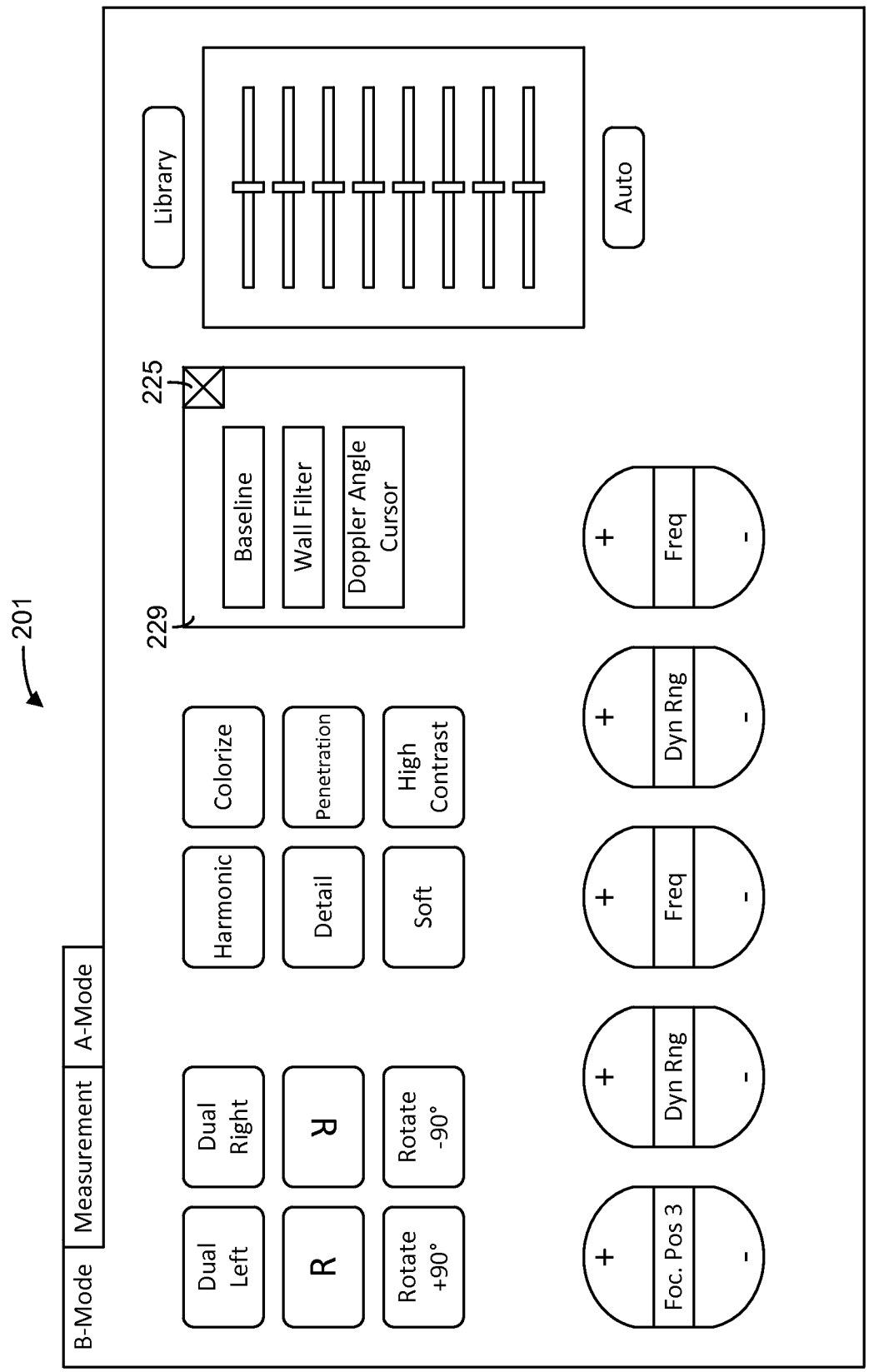
FIG. 4C illustrates an embodiment of a touchscreen user interface having a folder.

With reference to FIGS. 4A and 4C, the content of folder 227 may be displayed as a daughter dialog. In other embodiments, after being pressed, folder 227 is a window displayed over all or a portion of the display associated with tab 203 and the currently selected function. Opened folder 227 may cover some widgets but leave other widgets unobscured.

Opened folder 229 includes additional widgets. Opened folder 229 may include widgets such as buttons 211 and/or radio buttons 213. In some embodiments, opened folder 229 may further include continuous controls 205, sliders 221, text boxes, hyperlinks, drop-down lists, list boxes, combo boxes, check boxes, cycle buttons, datagrids, etc. A user may provide an input by pressing a widget or otherwise controlling the widget through opened folder 229.

In some embodiments, a user has the option of moving opened folder 229 to various positions on the screen. Opened folder 229 may be moved by pressing and holding opened folder 229 and dragging opened folder 229 to the desired position. In some embodiments, a user may press and hold anywhere on opened folder 229. In other embodiments, a user must press and hold a portion of opened folder 229 that is not overlaid by a widget. In further embodiments, opened folder 229 may include a header section which a user may press and hold while dragging to position opened folder 229.

In additional embodiments, a user is able to resize opened folder 229. A user may resize opened folder 229 by pinching or expanding with two fingers pressing a portion of opened folder 229. In other embodiments, one or more buttons are provided to allow a user to select from pre-determined sizes of opened folder 229 or to resize opened folder 229 to a custom size. In some embodiments, opened folder 229 may include one or more scroll bars which allow a user to access additional widgets. A user may navigate through opened folder 229 by pressing on the scroll bar. In other embodiments, a user may navigate through opened folder 229 by swiping a finger in the direction the user wants to scroll. In further embodiments, opened folder 229 includes pages of widgets. Each page may be organized according to a common scheme. For example, widgets may be organized alphabetically, according to frequency of use, by category of control, by type of widget (e.g., buttons, radio buttons, sliders, etc.), etc. In some embodiments, pages may be viewed by swiping a finger.

In one embodiment, a user exits opened folder 229 and returns to the screen by pressing a close button 225. In some embodiments, a user exits opened folder 229 by pressing folder 227 while opened folder 229 is displayed. In other embodiments, a user exits opened folder 229 by pressing anywhere outside of opened folder 229 (e.g., pressing a portion of the screen not overlaid by opened folder 229). In further embodiments, a user is returned to the screen and sub-opened folder 229 is closed once a user presses a widget or otherwise uses a control in opened folder 229. In alternative embodiments, one or more of the above exit configurations may be used in combination with other exit configurations.

Now with reference generally to FIGS. 4A-4C, some or all widgets may be programmed to exhibit similar or identical behavior or characteristics. When a widget is pressed by a user, the widget may change its appearance. For example, the color, shape, size, label, etc. of a widget may change temporarily to indicate to a user that the widget has been pressed. In other embodiments, the characteristic of the widget may change to signify that a parameter value has been changed, the widget is selected (e.g., in the case of a radio button), etc. In such a case, the widget may revert to its original characteristics following an event such as the selection of a different radio button, a return to default values, etc. A widget may also display a label identifying the widget and/or a value corresponding to the parameter the widget controls. For example, a widget may contain a label within the graphic representation of the widget. The widget may also display the current value of a parameter associated with the widget within the graphic representation of the widget. A widget may also have a disabled state in which the widget is displayed in a visually distinct manner and does not respond to attempted user inputs. For example, when a particular widget is incompatible with another currently selected widget, with the current values of certain parameters, etc. the widget may be disabled by processing circuit 163. The widget may then cease to respond to attempted user inputs until the widget is enabled by processing circuit 163. Touchscreen UI 201 may inform a user of a disabled widget by changing the visual characteristics of the widget. For example, a disabled widget may be greyed out, crossed out, shaded, displayed with a differently colored background, change size or shape, etc. The disabled widget appears visual distinct from an enabled widget. A widget may also be repositioned within touchscreen UI 201. A user may press and hold a widget for an extended time (e.g., 2 seconds) which switches touchscreen UI 201 into a customization mode. The user may then drag a widget to a new location including moving the widget back into the library of widgets.

The above description of possible configurations of touchscreen UI 201 is illustrative only. In further embodiments of the invention, different layouts of widgets, different numbers of widget types, etc. may vary from the discussed layouts. Similarly, touchscreen UI 201 may be implemented on hardware other than touchscreen 120. For example, touchscreen UI 201 may be implemented on one or more of touchpad or touchscreen 110, main screen 130, and an additional or peripheral input device. For example, touchscreen UI 201 may be implemented on a computing device remote from portable ultrasound system 100 but configured to control it through a communications connection. In some embodiments, touchscreen UI 201 may be implemented on a touch enabled remote device. In other embodiments, touchscreen UI 201 may be implemented virtually on a non-touch enabled remote device. For example, input through a virtually implemented touchscreen UI 201 may be accomplished using a mouse or other pointer device.

The above described widgets and features of touchscreen UI 201 may be customized by a user. In some embodiments, a user may enter a customization mode by pressing and holding a widget. In other embodiments, other gestures, as described herein, may activate a customization mode. In further embodiments, a user may customize touchscreen UI 201 by pressing a dedicated button 211 or tab 203 which allows for customization. In alternative embodiments, customization may take place through a menu or other listing of option. Customization of touchscreen UI 201 may alter characteristics such as the widgets on a screen associated with a particular function and/or tab 203, the action taken in response to particular gestures, default values for parameters and/or controls, selection of a particular embodiment as pertains to the function of a widget (e.g., how a vertical swipe affects DGC widget 219), information which is displayed (e.g., if current value labels are displayed corresponding to widgets), identification schemes (e.g., how related radio buttons 213 are identified), etc. In some embodiments, a user may snapshot the current configuration of widgets for a function as a preset for future use. A user may set all default parameter values and widget configurations using the snapshot. In other embodiments, the snapshot may allow for multiple customized configurations for a function which a user may switch between. A different configuration may form the presets/defaults for different types of examinations using the same function. In further embodiments, preset configurations may be stored for multiple users so that each user of portable ultrasound system 100 may configure the touchscreen UI 201 to their preference. For example, different users may log in to portable ultrasound system 100 using different profiles. The defaults and/or customized screens may be different for each user. Advantageously, customization of the user interface of portable ultrasound system 100 through touchscreen UI 201 increases the efficiency with which portable ultrasound system 100 may be used. For example, customization allows often used functions to be located on the touchscreen while less often used functions may be located in the library. This gives a user quick access to often used functions. Different users can adjust the customization to their individual needs to increase their efficiency of use.

With reference to FIGS. 4A and 4C, a folder 227 and/or open folder 229 may be created during touchscreen UI 201 customization when one widget is dragged on top of another widget. In some embodiments, additional widgets may be added to folder 227 by dragging them onto folder 227 during touchscreen UI 201 customization. In other embodiments, additional widgets may be added to folder 227 during anytime by dragging the widget onto folder 227. In some embodiments, a user is prompted to name folder 227 following the creation of the folder. In further embodiments, a user may be prompted to rename a folder 227 if a user presses and holds the folder 227. In some embodiments of touchscreen UI 201, a user is prevented from creating folders 227 within other folders 227. In other embodiments, a user is allowed to create folders 227 within other folders 227. In further embodiments, some widgets, by type and/or associated function, are allowed to be stored in folders 227 within folders 227. In some embodiments, a user may not create folders within library sub-screen 223. In other embodiments, a user may create folders within library sub-screen 223.

With reference to FIGS. 5A and 5B, some functions may have more widgets that can fit on one screen associated with the corresponding tab 203 in some embodiments of touchscreen UI 201. Alternatively, a user may want to organize the placement of widgets based on personal preference. In these and other cases, the screen can include library button 217 described above. Library button 217 allows access to additional controls related to the selected tab 203 and function. Additionally, library button 217 allows for customization of the buttons which appear on the screen associated with tab 203 of the selected function. Referring now to FIG. 5A, touchscreen UI 201 is depicted with a user pressing library button 217. This is illustrated with the hatching on library button 217. Pressing library button 217 provides a user access to the additional controls referenced above in discussion of the available widgets and library button 217.

Referring now to FIG. 5B, touchscreen UI 201 is depicted following a user pressing library button 217. In response to a user pressing library button 217, sub-screen 223 is displayed in touchscreen UI 201.

Figure 5C:
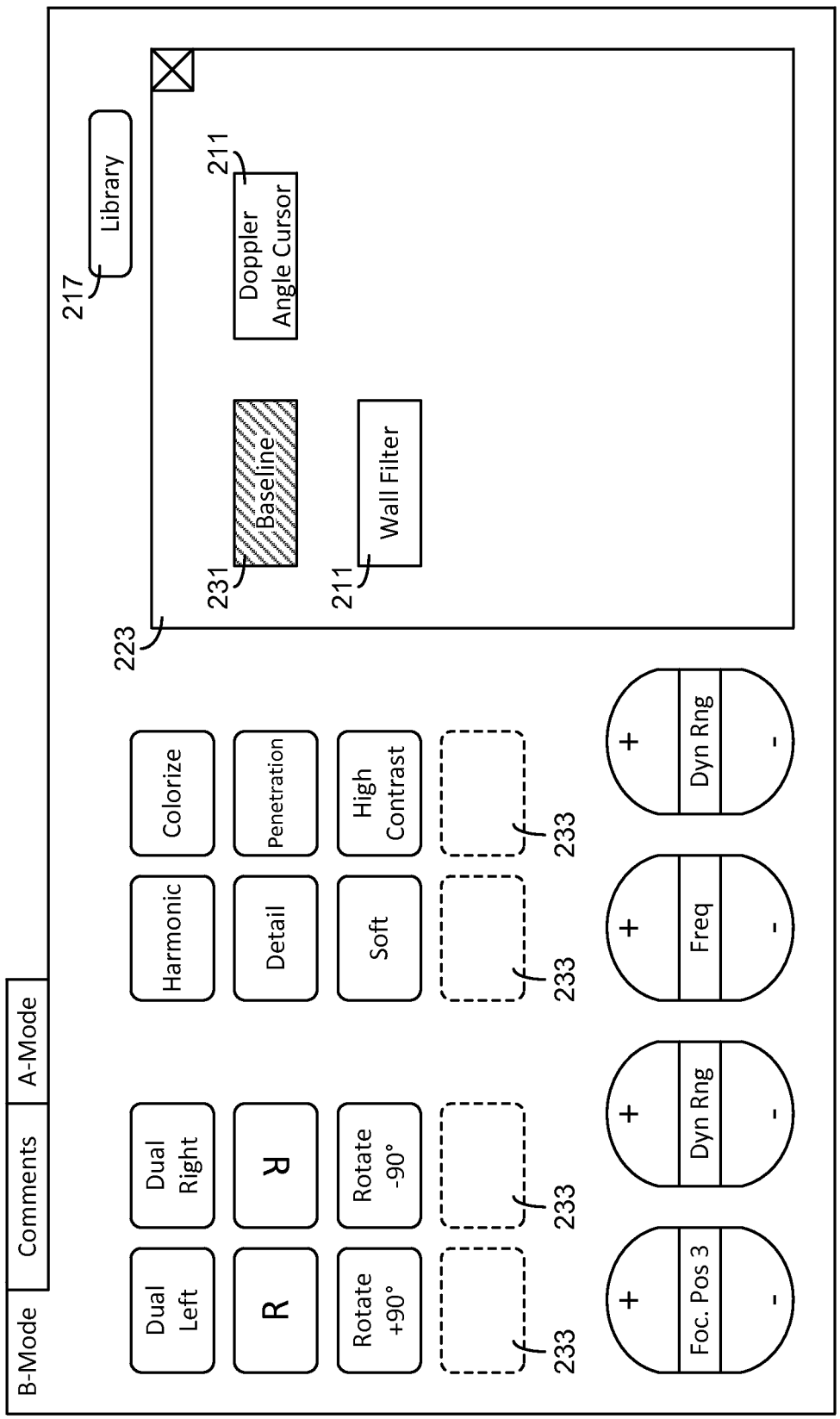
FIG. 5C illustrates customization of a user interface according to an exemplary embodiment.

Referring now to FIG. 5C, a user has entered customization mode for touchscreen UI 201. In one embodiment, a user enters customization mode by pressing and holding a button 231 (e.g., as indicated by shading) within sub-screen 223. A user may then drag a button 211 or the button 231 which was used to enter customization mode. Any widget may be positioned by dragging it. A user can drag a widget out of library sub-screen 223 on onto the screen associated with tab 203 and the related function. For example, a widget may be placed by dragging it to one of positions 233 (e.g., possible positions for the widget, in one embodiment, are illustrated with dashed outlines). In some embodiments, a user may remove a widget from the screen by dragging it onto sub-screen 223. In other embodiments, a user may remove a widget from the screen by dragging it off of the screen. In some embodiments, folders may not be created within library sub-screen 223. In some embodiments, the widgets in library sub-screen 223 may not be repositioned within library sub-screen 223. In other embodiments, widgets in library sub-screen 223 may be repositioned within library sub-screen 223. In further embodiments, a button may appear near or on each widget in customization mode which when pressed removes the widget from the screen.

Figure 5D:
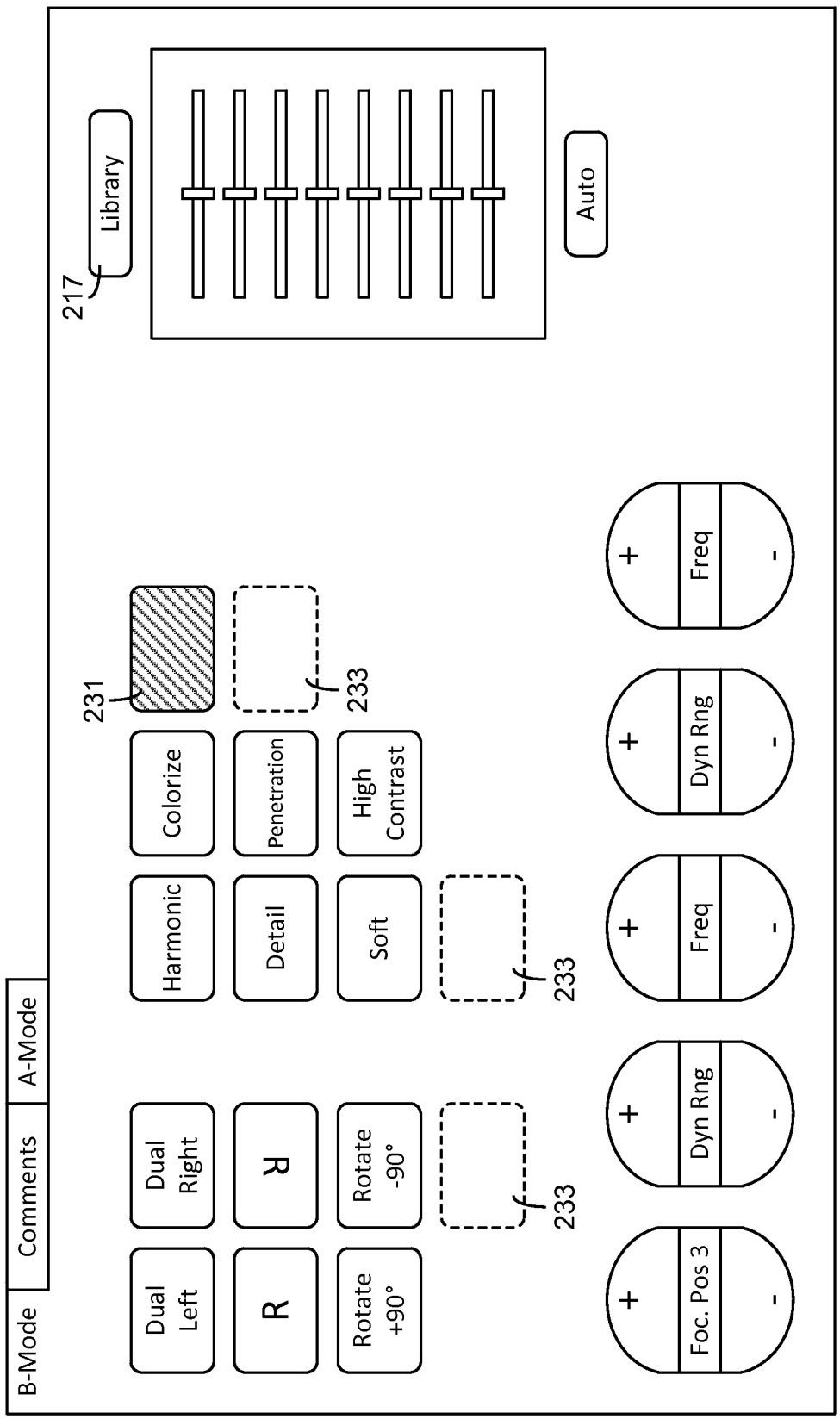
FIG. 5D illustrates entering a customization mode, according to one embodiment, by pressing and holding a button.

Referring now to FIG. 5D, a user may, in some embodiments, enter customization mode by pressing and holding a button 231 (e.g., as indicated by shading) on a screen associated with a tab 203 and corresponding function. In some embodiments, a user may initiate customization mode with library sub-screen 223 open or closed. A user may remove a widget from the screen by dragging it onto library button 217. In embodiments where customization mode is active while library sub-screen 223 is open, a user may remove a widget from the screen by dragging it onto sub-screen 223. In some embodiments, folders may not be created within library sub-screen 223. While in customization mode, a user may move a widget (e.g., button 231) to various locations on the screen. For example, button 231 may be moved to any of possible positions 233. In some embodiments, additional possible positions exist.

Referring generally to FIGS. 5A-5D, the widget to be repositioned or removed from the screen may be changed by pressing the desired widget while in customization mode. Pressing a widget selects that widget as the one to remove or reposition. In some embodiments, some widgets may not be removed and/or repositioned. For example, library button 217 may be fixed to one location on the screen. This may allow a user to easily find their way to all possible widgets related to a particular function. In some embodiments, adding a widget from library sub-screen 223 does not remove the widget from library sub-screen 223. The widget may be located in two places. In other embodiments, placing a widget from library sub-screen 223 onto the screen removes it from the list of widgets in library sub-screen 223. In some embodiments, a user may not move widgets between tabs 203.

In some embodiments, a user exits customization mode by pressing on the screen in a location not overlaid by a widget. By pressing in white space in the screen, touchscreen UI 201 exits customization mode and the user may interact with widgets according to the description previously provided. In other embodiments, a user may exit customization mode by performing other gestures described herein. For example, a user may exit customization mode by double pressing a widget, two finger swiping, pinching, expanding, etc. In additional embodiments, a user may exit customization mode by pressing library button 217. In still further embodiments, customization mode includes a button 211 which when pressed exits customization mode. This button 211 is removed from the screen automatically when the user is not in customization mode. In embodiments which include a button 211 dedicated to entering customization mode when pressed, pressing the same button 211 while in customization mode exits customization mode.

In some embodiments, some functions have only one instance of a customized screen. For example, particular functions may only have one tab 203 and corresponding screen of widgets. The customized screen appears the same for all exam modes while that function is selected. However, the set value controlled by each widget may be dependent on presets. For example, when a function is activated a parameter may be set at a default value. The parameter may be changed by a widget. In the case that the widget is not on the screen but is instead in library sub-screen 223, the widget may still be active or the associated parameter still have its default value even though the widget is not on the screen. A parameter which is adjusted by a widget may stay at the adjusted value while a function is active regardless of whether the widget is on the screen on in library sub-screen 223. For example, a user may switch between detail and penetration setting for several exam modes. For a thyroid exam the user may use the soft setting and rarely switches image type. The user may configure detail and penetration settings from the screen but still have the soft setting active for thyroid exams even through the widget is in library sub-screen 223. In some embodiments, a parameter controlled by a widget may return to a default or preset position when the function is exited. In other embodiments, the value of the parameter resets to the default value when the function is activated. In some embodiments, a parameter or mode set by a widget associated with one function may carry over to another function when a user switches functions via tab 203 or another method (e.g., hard buttons, touchpad or touchscreen 110 gestures, calling/activating a new function, etc.).

In additional embodiments, some functions may have more than one associated tab 203 and/or customized screen. In one embodiment, only the comments function, bodymarkers function, and measure function are allowed to have multiple customized screens.

Remaining features from client description here. Each preset value or default value may have its own customization.

In some embodiments, touchscreen UI 201 may prevent a user from repositioning and/or removing some widgets from the screen associated with tab 203 and a corresponding function. For example, the right side of the screen may be reserved for DGC widget 219, a time gain compensation widget, and/or an auto button (e.g., for automatically adjusting DGC widget 219, a time gain compensation widget, and/or other parameters and settings). In some embodiments, the right side of the screen is reserved for these widgets for all imaging functions but is not reserved for non-imaging functions (e.g., comment function, measure function, etc.). In additional embodiments, the bottom of the screen is reserved for continuous controls 205.

In some embodiments, certain widgets, when activated, may cause other widgets and/or controls to become unavailable. This may be communicated to a user by a widget or control appearing grayed out. When the widget is deactivated, the previously unavailable widgets and/or control may again become available to a user. This may be represented by a widget ceasing to be grayed out. For example, when a freeze widget is pressed, some pre-processing controls become unavailable. They may appear grayed out. Post-processing controls may remain available while the freeze widget is active. Pressing the freeze widget again or otherwise returning to the screen (e.g., by pressing outside a window generated by the freeze widget, pressing a widget not related to the freeze widget, pressing an exit button, etc.) reactivates the deactivated widgets.

In some embodiments, pressing a widget or otherwise interacting with a widget may cause additional widgets to be displayed to a user. In some embodiments, the additional widgets are displayed to a user on the screen in space not already filled by widgets. In other embodiments, the additional widgets may be displayed to a user in an additional window overlaying the screen and/or widgets on the screen. In further embodiments, some widgets may be temporarily removed from the screen and replaced with the additional widgets. The additional widgets may be removed and replaced with the originally displayed widgets upon the occurrence of an event (e.g., pressing one of the additional widgets, pressing a widget not removed from the screen, pressing a finish widget or exit widget, preforming a particular gesture, etc.).

For example, upon pressing the freeze widget additional cinematic controls (e.g., play button, pause button, scroll bar, etc.) become visible to a user. In cases in which there is sufficient room on the screen (e.g., a user has not filled all possible widget locations through customization of touchscreen UI 201), the additional cinematic controls are displayed in previously empty space on the screen. Preferably the additional cinematic controls are grouped together. In some embodiments, they may be located remote from one another. In cases in which there is not sufficient room for the additional cinematic controls, the additional cinematic controls may be displayed to a user in a window overlaying widgets and/or controls which are not used in conjunction with the freeze widget. Alternatively, the unrelated widgets may be temporarily removed and replaced by the cinematic control widgets as described above. In some embodiments, widgets are removed if the additional widgets may be grouped together when they replace the original widgets. If there is insufficient space or a configuration which does not allow this, the widgets may be displayed in a window as just described. In further embodiments, a user may set the behavior through the settings of touchscreen UI 201.

With reference to FIGS. 4, 6, 9, and 11, touchscreen UI 201 may interact with other hardware components of portable ultrasound system 100. The interaction between touchscreen UI 201, touchscreen 120, touchpad or touchscreen 110, keyboard 281, main screen 130, and/or additional controls may be managed by main circuit board 161 as explained previously herein with reference to FIG. 3. Inputs received through touchscreen 120 and touchscreen UI 201 may alter the displays of main screen 130 and/or touchpad or touchscreen 110. For example, changing a parameter through touchscreen UI 201 may alter the image displayed on main screen 130 (e.g., the addition of a comment). Changing an imaging mode, selecting a function, pressing a widget, etc. through touchscreen UI 201 may cause an illustration of a gesture to be displayed on touchpad or touchscreen 110. In some embodiments, hard key controls of keyboard 281 may have the same functionality as soft key widgets displayed through touchscreen UI 201 and/or gestures performed using touchpad or touchscreen 110. Providing an input through a hard key of keyboard 281 may update the display of a corresponding widget displayed by touchscreen UI 201, alter the image on main screen 130, etc.

Figure 6:
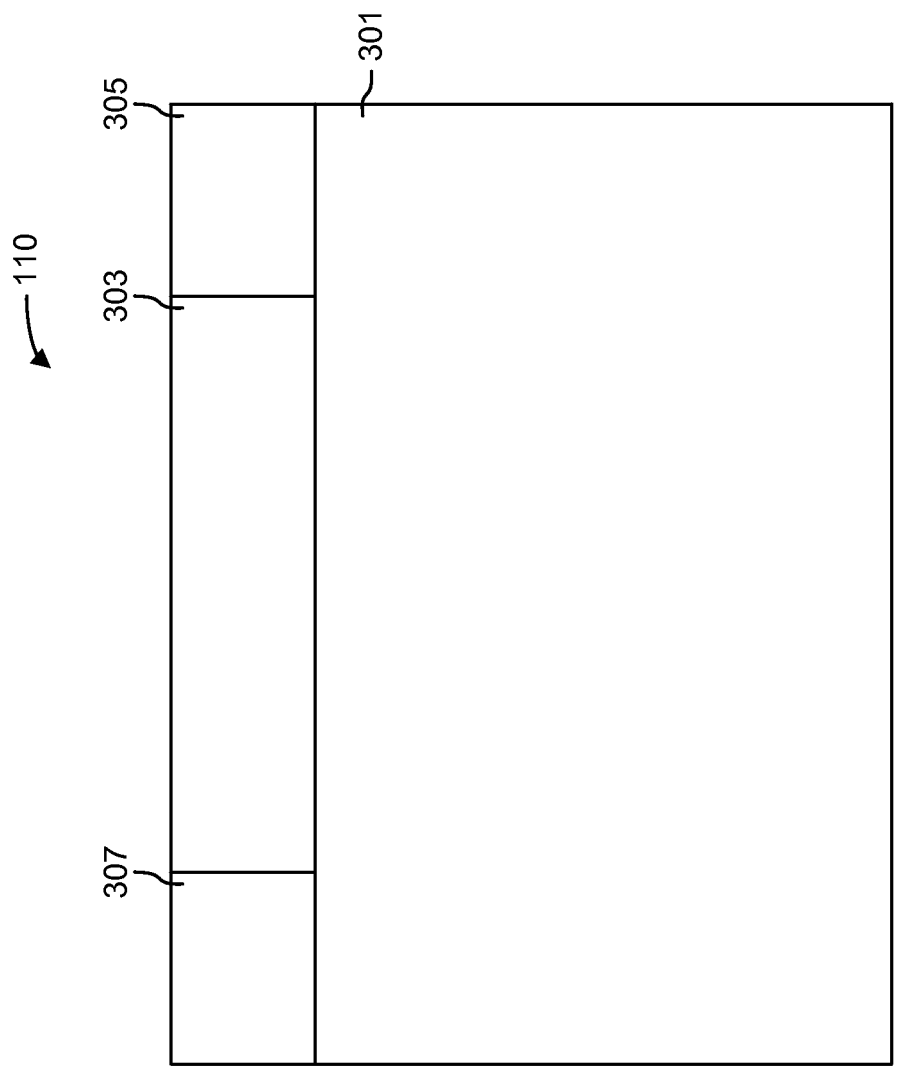
FIG. 6 illustrates an embodiment of a touchpad or touchscreen with multiple regions.

With reference to FIG. 6, some embodiments of portable ultrasound system 100 include touchpad or touchscreen 110. Touchpad or touchscreen 110 may allow a user to control on-screen user interface elements such as a region-of-interest cursor displayed on main screen 130 and used to navigate relative to particular areas of an ultrasound image and/or select particular regions. A user may also use touchpad or touchscreen 110 to manipulate a graphical user interface cursor used to select controls through touchscreen UI 201 displayed on touchscreen 120 (e.g., a user may use touchpad or touchscreen 110 to interact with widgets rather than pressing or performing gestures on touchscreen 120). In some embodiments, the cursor may allow interaction with elements on main screen 130. Touchpad or touchscreen 110 may also support multiple gestures. This includes single-finger swipes and presses and multiple-finger gestures.

For example, single-finger swipes may be used to change gain while imaging, scroll frame-by-frame through a paused clip of images, change the speed of a playing clip of images, etc. Continuing the example, multiple-finger gestures may include pinching in/out to zoom in/out on an image and/or area of interest, pinching in/out to change a Doppler gate size, two-finger rotation to change the angle-correct of a Doppler image, two-finger swipe to page through a series of images or scroll through a report, three-finger swipe to change context between live imaging and review of prior images, etc. In some embodiments the above described gestures may be supported by touchscreen 120 and/or 130 for the same and/or other functions. In further embodiments, any soft key which controls a continuous variable (e.g., continuous controls 205, siders 221, etc.) supports a single finger swipe gesture to adjust the variable. For example, volume or depth may be adjusted using a single finger swipe gesture in conjunction with a widget such as a slider 221 or continuous control 205. In additional embodiments, continuous variables may be adjusted by a gesture on touchpad or touchscreen 110 such as a single finger swipe. A soft key may nor may not be displayed on touchpad or touchscreen 110 during such an adjustment (e.g., a user may select a button to adjust the volume using keyboard 281 or touchscreen 120 and adjust the volume using a gesture performed on touchpad or touchscreen 110).

In some embodiments, hard key controls of keyboard 281 and/or soft key widgets displayed through touchscreen UI 201 may have the same functionality as gestures performed using touchpad or touchscreen 110. In other embodiments hard key controls of keyboard 281, gestures performed on touchpad or touchscreen 110, and/or soft key widgets displayed through touchscreen UI 201 provide redundant control of portable ultrasound system 100. A user may control an aspect of portable ultrasound system 100 through any of the three input methods/devices. This may provide a user who is unfamiliar with gesture controls an alternative to controlling the system with gestures. Redundant control schemes may also allow a user to learnt to control portable ultrasound system 100 more quickly and/or with greater efficiency.

With continued reference to FIG. 6, some embodiments of touchpad or touchscreen 110 include multiple regions. Touchpad or touchscreen 110 may include trackball region 301, swipe region 303, continue region 305, and/or complete region 307. Trackball region 301 may be used like a convention ultrasound trackball. For example, trackball region 301 may be used to position cursors on images displayed on main screen 130, interact with touchscreen UI 201 on touchscreen 120, position a region-of-interest, etc. Advantageously, a user may also perform gestures within trackball region 301 for carrying out more complex control of portable ultrasound system 100 such as the operation described above. For example, a user may use a two-finger pinch to expand or contract the region of interest (e.g., in zoom or CD widgets/functions), a two-finger pinch may expand or contract a gate used for measuring blood flow (e.g., while the PW function is selected), a two-finger twist may change the angle of a gate while the PW function is selected, etc. Including traditional pointing and positing operations along with more complex gesture controls on a single input device allows a user greater control over portable ultrasound system 100 without requiring multiple input devices and/or multiple hands to be used. A user may exercise greater control over portable ultrasound system 100 while simultaneously using a probe with their free hand. In some embodiments, gesture interactions, such as the ones described above, are redundant with traditional button interactions. Advantageously, this allows a user unfamiliar with the gesture controls to perform the same functions using traditional controls.

In some embodiments, touchpad or touchscreen 110 displays an image of a traditional trackball in trackball region 301. This may indicate to a user that gestures performed in trackball region 301 provide functions similar to that of a traditional trackball. For example, moving a finger on trackball region 301 may provide x-y position movement of a cursor. In some embodiments, the color green on main screen 130 is reserved to indicate the widget or GUI feature attached to trackball region 301. The color green indicates to the user that trackball region 301 controls the GUI element colored green. For example, if an item is green it will move as a user drags their finger across trackball region 301. In further example, if there is a caliper pair (e.g., for blood flow measurement), the side that is attached to trackball region 301 is green while the other side is white. This indicates to a user which side of the caliper pair will move in response to input using trackball region 301. As an additional example, while the triplex imaging function is selected, with the Doppler cursor of the CD pan box is green, but not both. In some embodiments, only a single GUI element is attached to trackball region 301 at a time. In other embodiments, multiple GUI elements may be attached to trackball region 301 at a time.

Swipe region 303 is a strip along the top of touchpad or touchscreen 110 which allows for a user to interact with portable ultrasound system 100 through horizontal gestures independent on trackball region 301. Swipe region 303 allows for two separate gesture input regions on touchpad or touchscreen 110 simultaneously (e.g., one gesture can be made on trackball region 301 while the other is made on swipe region 303). In some embodiments, one gesture may be made in swipe region 303 while a second gesture is made at the same time in trackball region 301. For example, a user can scroll back and forth through a clip of images using swipe region 303 (e.g., using left to right swipes and right to left swipes) while also controlling a measurement caliper using trackball region 301. A user is allowed to quickly measure the same feature of multiple images or multiple features over multiple images. This saves time and allows for easy, efficient use of portable ultrasound system 100. Simultaneous control may be used in conjunction with other functions and/or imaging tasks performed by portable ultrasound system 100.

In other embodiments, one gesture may have different effects depending on whether it is made in swipe region 303 or trackball region 301. This may allow a user greater control options with a limited number of gestures. Each gesture may have two effects depending on which region of touchpad or touchscreen 110 the gesture is made. This expands the number of interactions available to a user through gesture control. For example, a horizontal swipe from left to right using one finger may move a cursor if performed in trackball region 301 while the same gesture may move from a first image to a second image when viewing multiple images if performed in swipe region 303. In some embodiments, swipe region 303 supports gestures other than swipes. In other embodiments, swipe region 303 only supports swipe gestures (e.g., single-finger swipe, two-finger swipe, three-finger swipe, etc.). In some embodiments, the point at which touchpad or touchscreen 110 and keyboard 281 meet provides a tactile landmark to a user. This may allow a user to easily find swipe region 303 (e.g., just below the point at which keyboard 281 ends and touchpad or touchscreen 110 begins). This may be advantageous because a user can find swipe region 303 without taking their eyes away from either main screen 130 or touchscreen 120. Similarly, a tactile landmark such as the one described may allow a user to more easily locate swipe region 303 in instances of poor visibility.

Swipe region 303 and gestures performed in swipe region 303 may have different effects depending on the selected function and/or widget. For example, in live imaging (e.g., when the B-mode function is selected) swipe region 303 may be used for gain control (e.g., swiping left-to-right to increase gain and right-to-left to decrease gain). This may be redundant with a gain paddle but may allow for a faster sweep through a large range of gain. While a video or series of images is frozen (e.g., by the freeze widget), swipe region 303 may provide for frame-by-frame review (e.g., a swipe advances the video a single frame). As additional example, a rapid swipe in swipe region 303 may play or pause a video or series of images.

Continue region 305 and complete region 307 control portable ultrasound system 100 in a similar manner across different functions and tasks. In other embodiments, continue region 305 and complete region 307 may have different and/or unique effects for different functions and/or tasks. Continue region 305 allows a user to cycle between peer choices. A user may switch between options or choices in a group of like options or choices by pressing touchpad or touchscreen 110 in continue region 305. For example, pressing in continue region 305 may switch between controlling the left or right side of a caliper pair. In such a case (e.g., toggling the active side of a caliper pair), touchpad or touchscreen 110 may display the word "Set" in continue region 305 to indicate this function to a user. As an additional example, continue region 305 may be labeled "Update" and toggle between simultaneous imaging and updating the display (e.g., during PW-mode imaging). Continue region 305 may allow a user to cycle between peer choices which depend on the currently selected function or currently active widget. For example, pressing in continue region 305 may switch between changing the size or position of a region of interest through trackball region 301. In some embodiments, continue region 305 may be redundant of other controls and/or regions. For example, while the zoom or CD function/widget is selected, continue region 305 may be labeled "Poz/Size" and be redundant with the position and sizing gestures and regions described above.

Complete region 307 allows a user to finish a task and move on to a new task. For example, pressing touchpad or touchscreen 110 in complete region 307 may be an event which exits a selected function, deactivates a widget, closes a window, etc. In some embodiments, complete region 307 may also serve as an enter mechanism. For example, pressing touchpad or touchscreen 110 in complete region 307 may enter a caliper measurement into a result database. Touchpad or touchscreen 110 may display the word "Enter" in complete region 307 to indicate to the user the function of complete region 307. As an additional example, in Doppler cursor mode, complete region 307 may be labeled "PW" and invoke the strip mode when pressed by a user.

Figure 7:
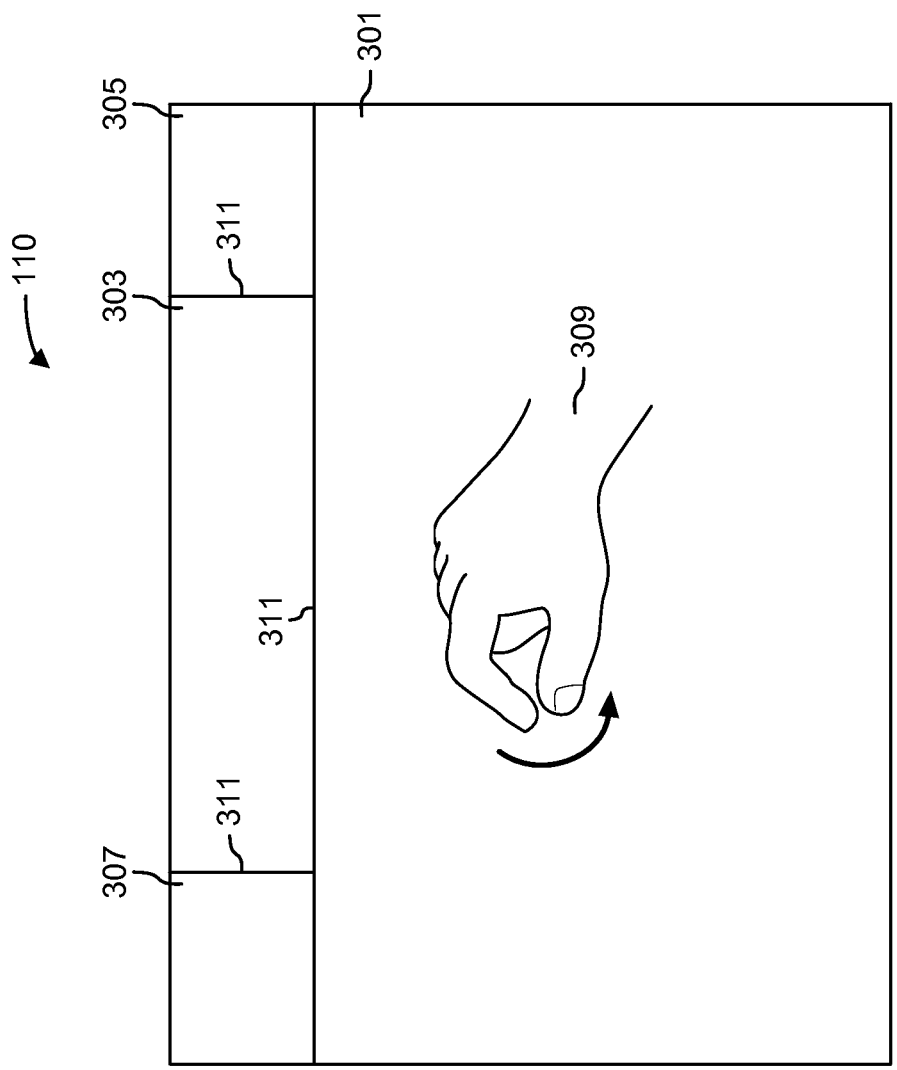
FIG. 7 illustrates gesture input using a touchpad or touchscreen according to an exemplary embodiment.

Referring now to FIG. 7, touchpad or touchscreen 110 is a touchscreen which allows for touch inputs as well as the display of images in some embodiments. In such a case, touchscreen UI 201 and/or main circuit board 161 may control the images displayed on touchpad or touchscreen 110 as explained previously. Touchscreen UI and/or the functions described herein may be implemented as computer code stored in memory 165 of portable ultrasound system 100 and executed by processing circuit 161. Touchpad or touchscreen 110 may provide visual feedback to a user and may provide prompts about the user interface. For example, touchpad or touchscreen 110 may indicate that an input has been received by displaying an image (e.g., a green checkmark, circle, field of a single color, etc.). In some embodiments, the regions described above are illustrated by visually distinguishing images on touchpad or touchscreen 110. For example, each region may be a different color or each region may be separated with by lines 311 delineating each region. In some embodiments, touchpad or touchscreen 110 may display gesture illustration 309. Gesture illustration 309 may be an image or animation which illustrates to a user how to perform a control gesture. In some embodiments, gesture illustration 309 includes text which explains how to perform the gesture and/or what the gesture controls. In additional embodiments, gesture illustration 309 may be an animation which illustrates the gesture being performed and illustrates the resulting response to the input (e.g., illustrates a gesture moving a cursor followed by the cursor being moved on a screen). Gesture illustration 309 may assist a new user in learning gesture controls for portable ultrasound system 100. In additional embodiments, touchpad or touchscreen 110 may be illuminated to allow for use of touchpad or touchscreen 110 in low light or decreased visibility. Touchpad or touchscreen 110 can provide further visual information in other embodiments. For example, touchpad or touchscreen 110 can provide visual information discussed throughout with respect to main screen 130 and touchscreen 120.

Figure 8:
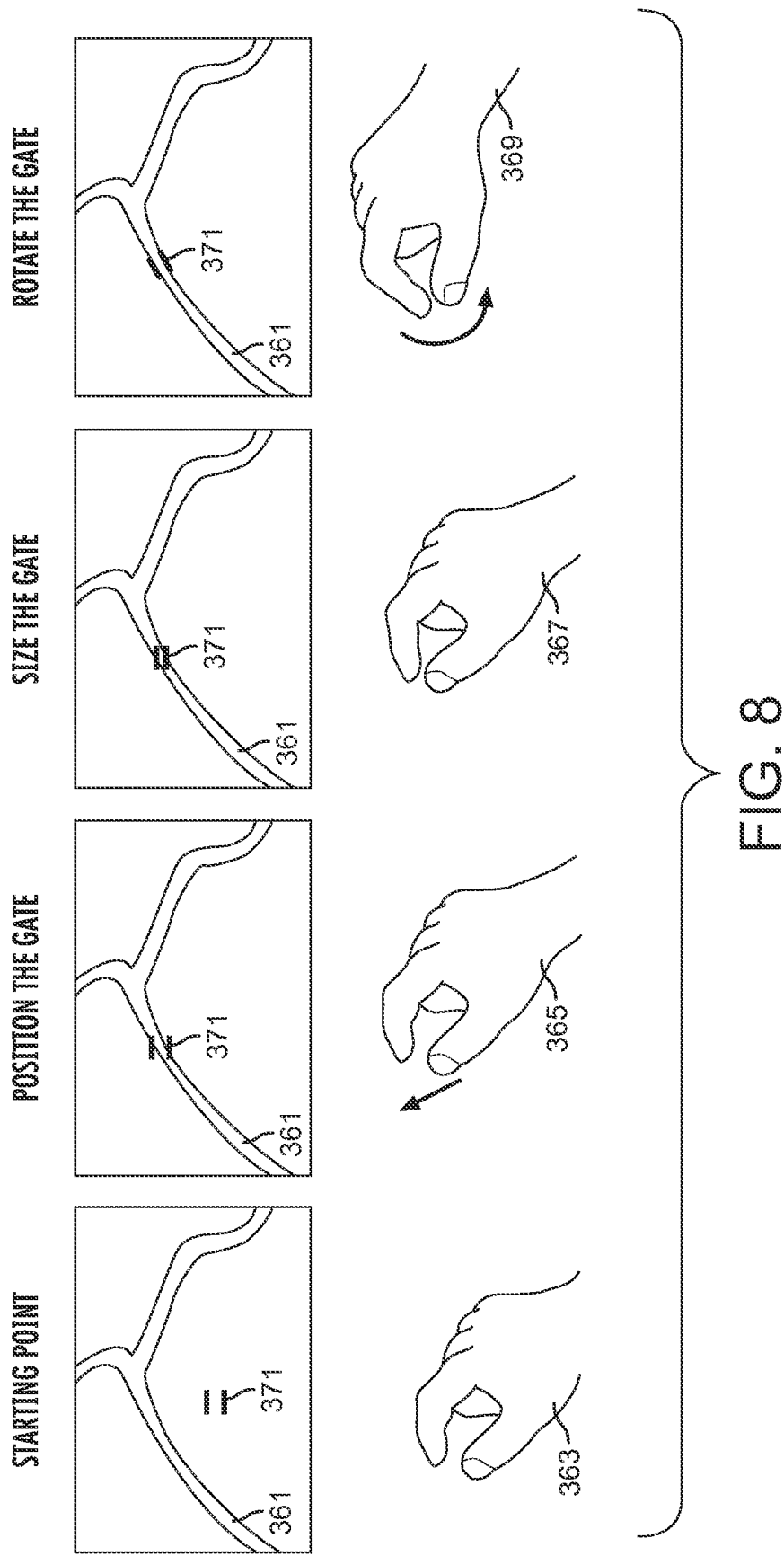
FIG. 8 illustrates a plurality of gestures a user may perform in conjunction with a touchpad or touchscreen according to an exemplary embodiment.

FIG. 8 illustrates gesture control, of the type discussed above, of portable ultrasound system 100 during the task of blood flow analysis. Ultrasound examinations may include measuring the blood flow in a vessel 361. An operator positions gate 371 on the vessel 361 for which blood flow is to be measured. In order to align the gate 371 with vessel 361, an operator adjusts the position of gate 371, the size of gate 371, and/or the angle of gate 371. Portable ultrasound system 100 replaces the traditional controls for adjusting these parameters (e.g., knobs) with gestures performed on touchpad or touchscreen 110. This has the advantage of allowing a user to align gate 371 with a single hand. The user is also able to adjust position, size, and/or angle simultaneously (e.g., a user performs multiple gestures at the same time). One control device may be used rather than three. In some embodiments, only two fingers are required to align gate 371. Two finger gesture control may be more efficient by requiring a user to operate fewer input devices. Two finger gesture control may be more intuitive to a user by allowing a user to position two sides of gate 371 by moving each finger.

A user enters a mode for blood flow analysis. An image of vessel 361 is displayed to the user. The image may be displayed on one or more of main screen 130, touchscreen 120, or touchpad or touchscreen 110. A user places two fingers 363 on touchpad or touchscreen 110 to place gate 371 at the starting point. The gate 371 icon appears on main screen 130 and/or touchscreen 120 in a location corresponding to the relative location of the user's fingers on touchpad or touchscreen 110. The user positions gate 365 by dragging two fingers 365. Gate 371 moves in the direction corresponding to the direction in which the user's fingers move. By dragging two fingers 365 in any direction, a user is able to position gate 371 over vessel 361. A user pinches in or out with two fingers 367 in order to size gate 371. Pinching in (e.g., bringing the two fingers closer together) reduces the distance between the two parallel lines of gate 371. Pinching out (e.g., moving the two fingers further apart) increases the distance between the two parallel lines of gate 371. A user moves two fingers in a rotational manner 369 to change the angle of gate 371. Rotating two fingers 369 counter clockwise (as depicted) rotates gate 371 counter clockwise. Rotating two fingers 369 clockwise rotates gate 371 clockwise. A user may rotate gate 371 with these gestures to change the angle of gate 371 to be parallel with the primary orientation angle of vessel 361.

The above described gestures may be performed simultaneously. For example, while dragging two fingers 365 to position gate 371 a user may also be pinching in or out with two fingers 367 to adjust the size of gate 371. In some embodiments, there is no limit to the number of gestures which may be performed simultaneously (e.g., a user may position, size, and rotate gate 371 all a the same time). The changes in gate 371 due to a user's gestures described above are reflected on the screen displaying the image of vessel 361 and gate 371. As a user performs gestures, the image may be continuously updated.

In other embodiments, the above described gestures may be performed using touchscreen 120 and/or main screen 130 to position gate 371. For example, the image of vessel 361 may be displayed on all or part of touchscreen 120 with the user performing the above described gestures on touch screen 120 to position gate 371. In additional embodiments, different gestures may be used to adjust the size, position, and/or angle of gate 371. In further embodiments of portable ultrasound system 100, hard key controls (e.g., knobs) may provide an additional way for a user to align gate 371. In some embodiments, the image vessel 361 may appear on touchpad or touchscreen 110 instead of or in addition to main screen 130 and/or touchscreen 120.

Figure 9:
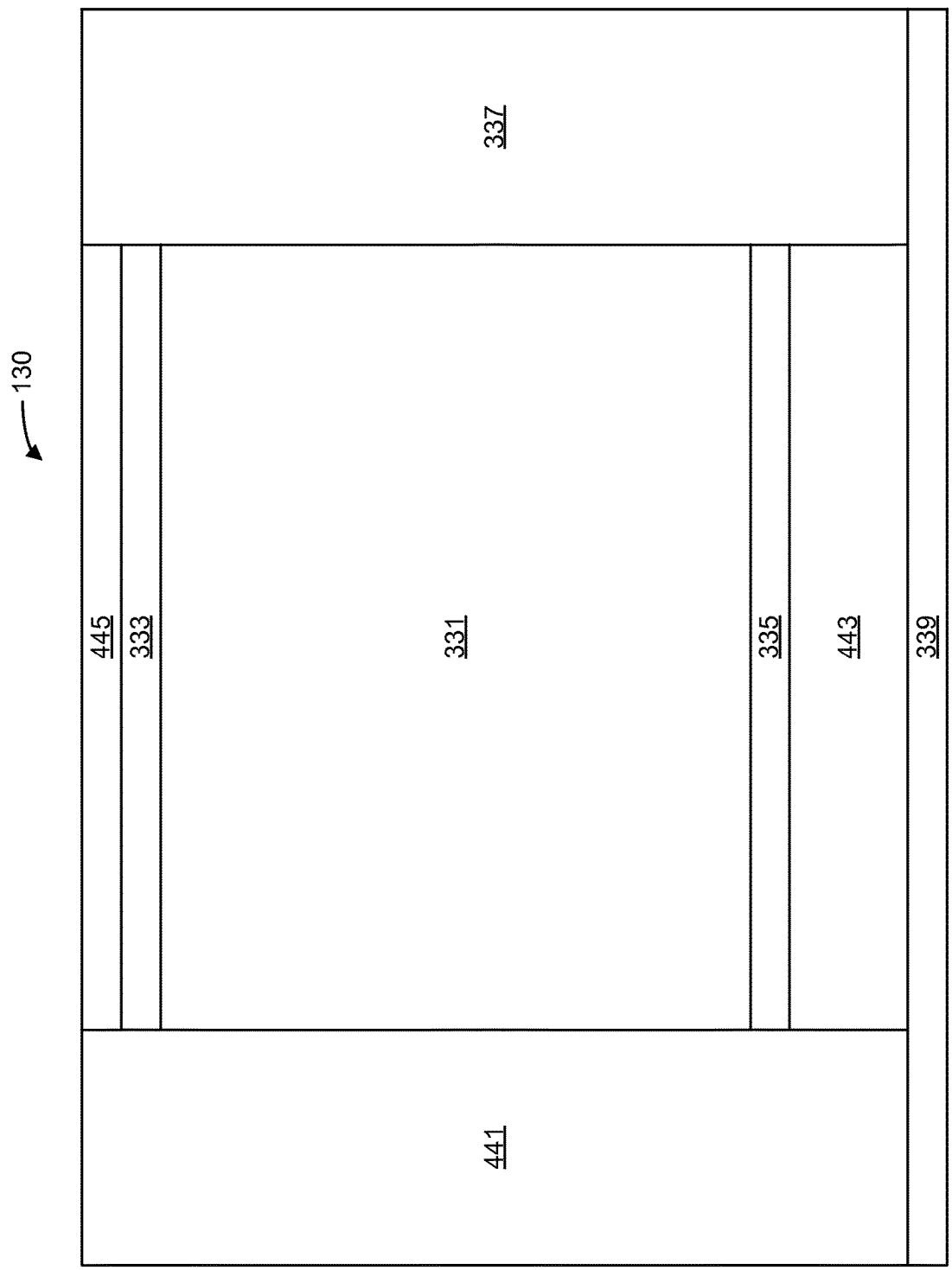
FIG. 9 illustrates an embodiment of a main screen having multiple fields.

FIG. 9 illustrates an embodiment of main screen 130. Main screen 130 may be divided into one or more fields. Each field may display information of a different type. In some embodiments, different fields are visually differentiated. Fields may be separated with borders and/or lines. In some embodiments, different fields have different background colors, font colors, font sizes, font types, etc.

Image display field 331 may display an image of the patient generated using ultrasound. In some embodiments, measurement results and/or parameter values are displayed with the image in image display field 331. For example, information may be placed adjacent to an image in image display field 331 (e.g., information is fit to the image such as in the upper left and upper right when the ultrasound probe is a convex probe or phased array probe). In other embodiments, image display field 331 only displays an image of the patient generated by ultrasound. In some embodiments, image display field 331 has a width of 1024 pixels and a height of 722 pixels. Information field 333 contains information such as patient name, identification information, date, institution name, etc. In some embodiments, image display field 331 and information field 333 form the area of main screen 130 which may be stored by a user as a recorded image. For example, a user may store an image or video clip of image display field 331 and information field 333 using controls of portable ultrasound system 100. These controls may be widgets associated with touchscreen UI 201, hard key controls of keyboard 281, gestures, etc. In other embodiments, all of main screen 130 may be stored as an image or video. In further embodiments, the fields which are recorded may be selected by a user.

Cinematic bar field 335 provides information related to a particular image within a set of images forming a video. Cinematic bar field 335 may also provide information regarding a video clip of ultrasound images. For example, information may include number of images in a clip, date the images were taken, duration of the clip, comments, etc. In some embodiments, cinematic bar field 335 is blank during live imaging.

Thumbnail field 337 displays the most recent captured static ultrasound images and/or ultrasound video clips. For example, thumbnail field 337 may display the prior three ultrasound images recorded by portable ultrasound system 100. In some embodiments, thumbnail field 337 only displays the image field 331 of recorded images. Information field 333 may be clipped on display. In other embodiments, thumbnail field 337 also displays information corresponding to each image.

Status bar field 339 displays status information to the user. For example, status bar field 339 may display information to the user regarding the currently active function of portable ultrasound system 100, whether images are being recorded, information regarding the patient being examined, etc. In some embodiments, status bar filed 339 is located across the bottom of main screen 130. Status bar field 339 can include icons and or data fields for conveying information to a user. For example, status bar field 339 can include a data field showing the number of images stored in the current exam, a battery icon illustrating the remaining amount of battery power with or without a listed remaining time or percentage, a network icon illustrating the presence or absence of a network connection, a wireless connection icon indicating signal strength of a wireless network connection, a printer icon, a help icon, and/or other icons or information. Mini report field 441 displays information to a user regarding entered data and associated calculation results. For example, mini report field 441 may show a list of entered data and relevant calculations for examinations involving measurements. Mini report field 441 can include a plurality of tabs with each tab associated with a different portion of the examination (e.g., a tab corresponding to each of a plurality of fetuses) or a different patient. The mini report field 441 can include a preset list of measurement that are configured by the user and may correspond with the type of examination in progress. The mini-report filed 441 can show the list of measurements that a user has selected as well as results for the measurements which have been performed during the examination. Measurements and or other information presented by mini-report filed 441 can pertain to any ultrasound examination type. For example, measurements presented by mini-report field 441 may pertain to measuring one or more fetuses and may include measurements such as biparietal diameter, head circumference, abdominal circumference, femur length, crown-rump length, humerus length, amniotic fluid volume, average ultrasound age, gestational age, estimated fetal weight, and or other measurements or information. Operation direction field 443 displays user interface prompts and messages to the user.

In other embodiments, main screen 130 does not have set fields for the display of various information. Main screen 130 may display information in a variety of configurations. In some embodiments, the way in which information is displayed (e.g., the position of each type of information on main screen 130) is customizable by the user. In one embodiment, a user may customize main screen 130 through menus of touchscreen UI 201 and/or portable ultrasound system 100. In another embodiment, a user may customize main screen 130 using touch inputs as described with reference to touchscreen UI 201.

Figure 10:
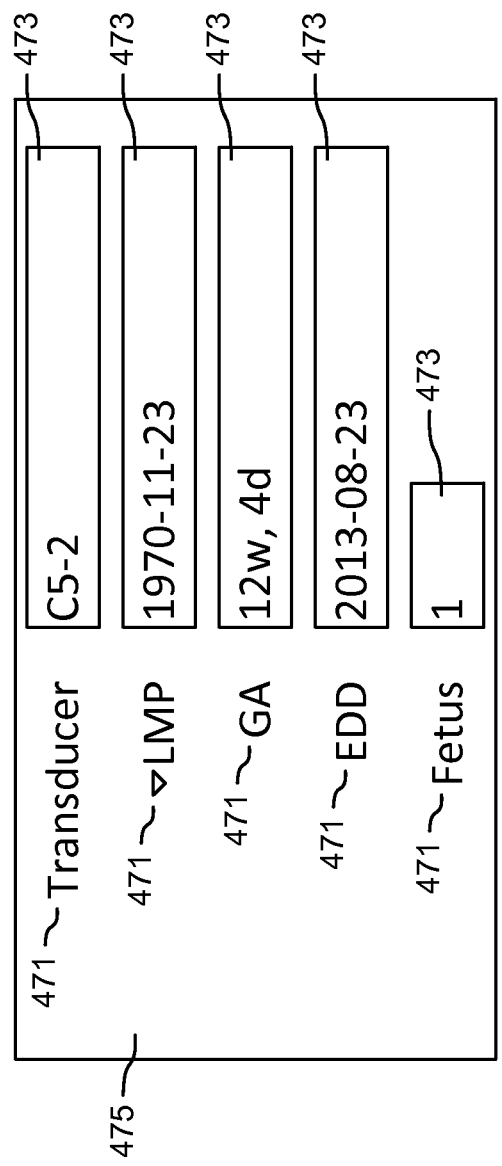
FIG. 10 illustrates an embodiment of information displayed on a main screen.

FIG. 10 illustrates an embodiment of information displayed on main screen 130. Information displayed on main screen 130 may include labels 471 and fields 473. In some embodiments, all labels all right justified. Labels may be generated by portable ultrasound system 100 to describe information displayed to a user in a field 473. In some embodiments, fields 473 may display information provided by a user. A user may, for fields 473 displaying user inputs, select a label 471 from a drop down menu of default labels. In other embodiments, a user may input a label 471 and/or edit an existing label. In some embodiments, all text fields 473 are left justified. In other embodiments, other alignments may be user. In some embodiments, all text is Arial bold font. In other embodiments, a different font may be used. In still further embodiments, multiple fonts may be used. For example, Arial may be used for text in fields 473 while Times New Roman is used for the text of labels 471. In some embodiments the background 475 is RGB color 40/48/60, the background of an editable field is RGB color 78/86/108, text in an editable field is RGB color 196/199/206, and label 471 text is RGB color 123/127/141.

A user may interact through additional user interface elements other than touchscreen 120, touchpad or touchscreen 110, and/or main screen 130. Some embodiments of portable ultrasound system 100 include keyboard 281. Keyboard 281 includes hard key controls dedicated to predefined functionality. Hard keys may include hard buttons 481, paddles 483, switches, knobs, etc. In some embodiments, keyboard 281 includes a full alphabet keyboard. Additional keys may also be included. For example, keyboard 281 may include an ANSI keyboard layout in addition to other hard key controls.

Figure 11:
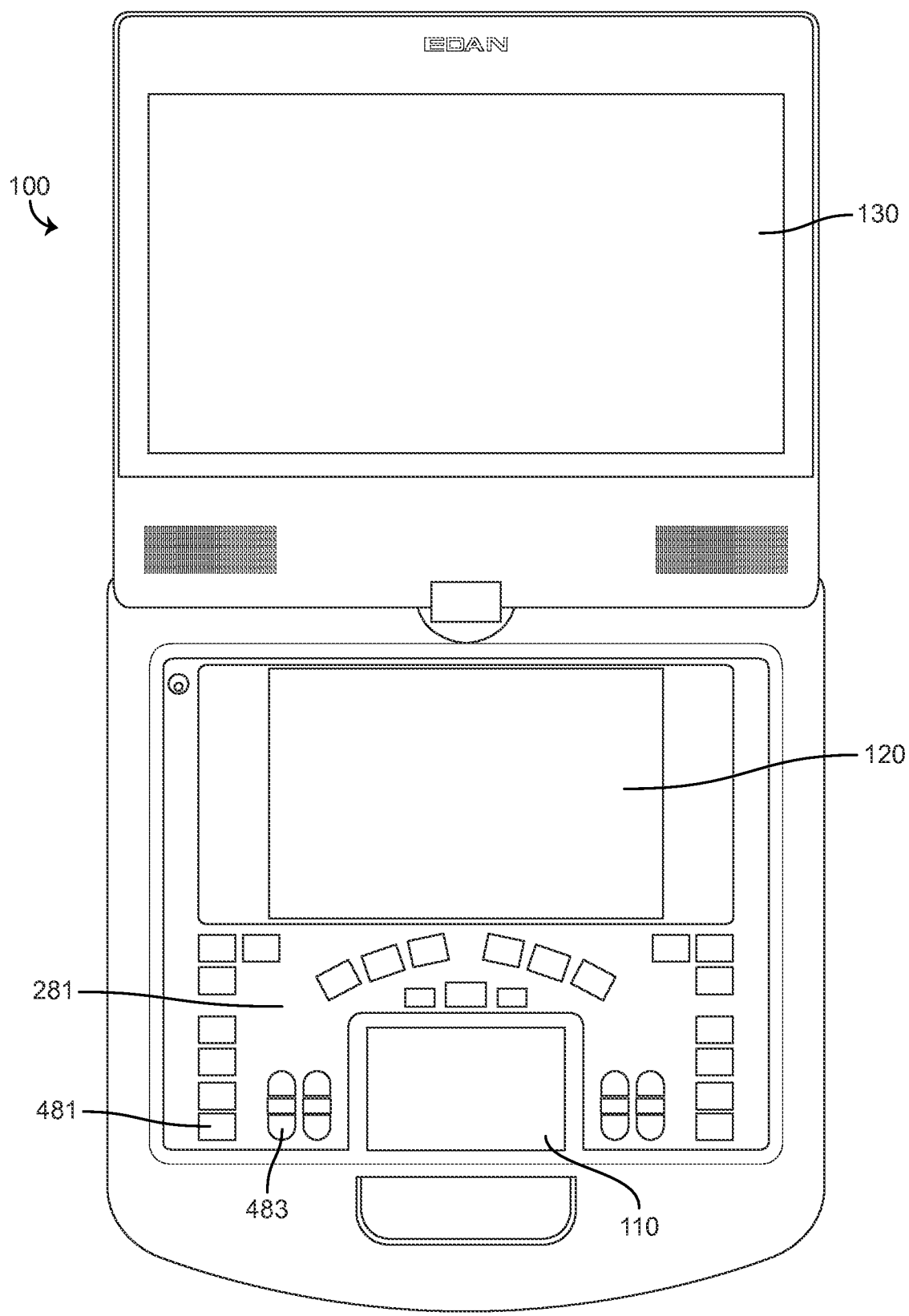
FIG. 11 illustrates an exemplary embodiment of a portable ultrasound system with a plurality of input and output devices.

Generally, systems resources such as the input and output devices discussed with reference to FIG. 11 are controlled by main circuit board 161 according to a function stack. Functions (e.g., B-mode imaging, Comment, Measurement, etc.) are assigned system resources (e.g., input devices, output devices, computational resources, etc.) according to the position of each function in the function stack. Using the function stack framework, main circuit board 161 allows for input devices to control elements of a single function at a time while still providing control for multiple functions. For example, touchpad or touchscreen 110 provides an input for only one function at a time but may provide input (e.g., moving a cursor) for different functions at different times (e.g., moving a cursor for commenting and later moving a cursor for measuring). The function stack framework described herein may be implemented as computer code stored in memory 165 and executed by processing circuit 163 of main circuit board 161.

A function is a user-invoked interaction that claims one or more resources. Examples of functions include B-mode, PW, Comments, Measurements, Review, etc. A function is active when it has been invoked (e.g., the function is running and displayed on touchscreen 120 with an associated tab 203). For example, B-mode is active upon power-up, but PW, Comments, etc. are not active until the appropriate button is pressed to invoke it. A function remains active until it is exited, either by a key press or in response to a system event. A function is selected by a user when it is activated or otherwise selected (e.g., by pressing a corresponding tab 203 for the function).

A resource is a defined UI input mechanism that can be used by one function at a time. Examples of resources include touchscreen 120, touchpad or touchscreen 110, keyboard 281, a peripheral device such as a mouse, etc. A input device may constitute multiple resources. For example, each region of touchpad or touchscreen 110 may be a different resource for the purposes of resource management using the function stack. In some embodiments, resources which are controlled via the function stack described herein also include output mechanisms and/or computing resources. For example, resources may include the output to the screen of touchpad or touchscreen 110, the output to the screen of touchscreen 120, the output to main screen 130, speakers, random access memory, hard disk memory, processors, etc.

When a function is invoked it generally takes ownership of any resources it is programmed to use. As other functions are invoked they in turn will take ownership of the resources they are programmed to use. Thus the currently active functions form a stack, where the function at the top of the stack owns all requested resources. Functions further down the stack own resources only to the extent they are not needed by functions higher in the stack. A mechanism exists for the user to change the order of the stack by moving a function to the top of the stack. A function is brought to the top of the function stack by being selected by a user (e.g., when a user selects a function using tab 203 through touchscreen UI 201 or activates a function).

Functions can change their requested resources in response to system events. For example, the B-mode function normally does not request the trackball resource, but it does when the image is zoomed. Changing requested resources does not change a function's position in the stack. Resources which are no longer requested become available to functions lower in the function stack. Resources which were previously not requested by the selected function which were owned by functions lower in the function stack become owned by the function higher in the function stack which requests the resource.

Imaging functions can become dormant in response to system events, such as invoking a measurement report or review screen. When imaging becomes dormant imaging stops but the entire imaging state, including the relative positions of imaging functions on the stack, is retained. In some embodiments, while in this state the imaging tabs are not displayed on the touchscreen and no imaging controls are active.

Figure 12:
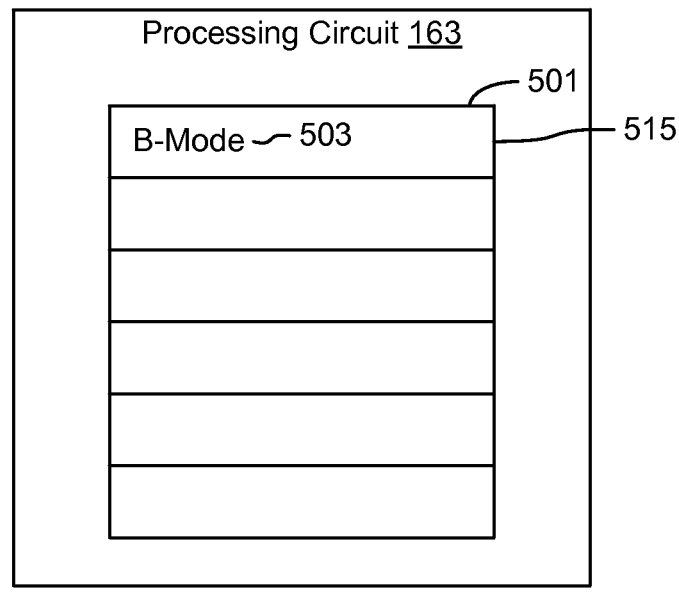
FIG. 12 illustrates a block diagram of an embodiment of a function stack for controlling functions and associated hardware resources.

FIG. 12 illustrates a block diagram of an embodiment of function stack 515 as implemented by processing circuit 163. Function stack 515 may be implemented as computer code executed by processing circuit 163. Processing circuit 163 may manage input and output of portable ultrasound device 100 according to function stack 515. Processing circuit 163 may control input devices and output devices using one or more display interfaces 171 and user input interfaces 173. Additional control may be possible through the various components of main circuit board 161 described with reference to FIG. 3.

In some embodiments, B-mode function 503 is activated upon start-up of portable ultrasound system 100. Upon activation, a function is moved to the highest position 515 of function stack 501. Thus, the function in the highest position 515 controls all requested resources as implemented by processing circuit 163. Un-requested resources remain available to functions lover in function stack 501.

Figure 13A:
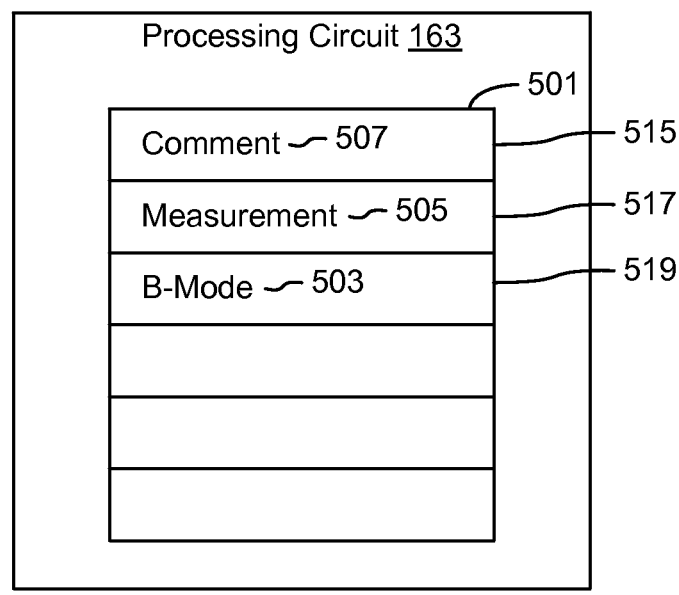
FIG. 13A illustrates the addition of activated functions to the function stack according to an exemplary embodiment.

Now with reference to FIG. 13A, as additional functions are activated, they are added to function stack 501. For example, FIG. 13A depicts a situation in which after start-up a user has activated measurement function 505 and then comment function 507. As comment function 507 is the most recently activated function and the user has not switched between active functions, comment function occupies the highest potion 515 in function stack 501. Similarly, measurement function 505 as the second most recently activated function is in the second position 517 of function stack 501. B-mode function 503 occupies the third position 519. B-mode function is allowed to control and receive input from resources not requested or owned by functions in highest position 515 and second position 517. For example, comment function 515 may request touchscreen 120 and trackball region 301. As the highest function in function stack 501, processing circuit 163 assigns those resources to comment function 507. Measurement function 505 may request keyboard 281 and trackball region 301. Processing circuit 163 has assigned trackball region 301 to comment function 507 and since it is higher in the function stack comment function retains ownership of trackball region 301. Measurement function 505 is assigned keyboard 281 by processing circuit 163 because no function higher in function stack 501 has requested the resource. Processing circuit 163 assigns any un-owned resources that B-mode function 503 requests to B-mode function 503. B-mode 503 may not have ownership of trackball region 301, touchscreen 120, or keyboard 281 because functions higher in function stack 501 have requested the resources.

Figure 13B:
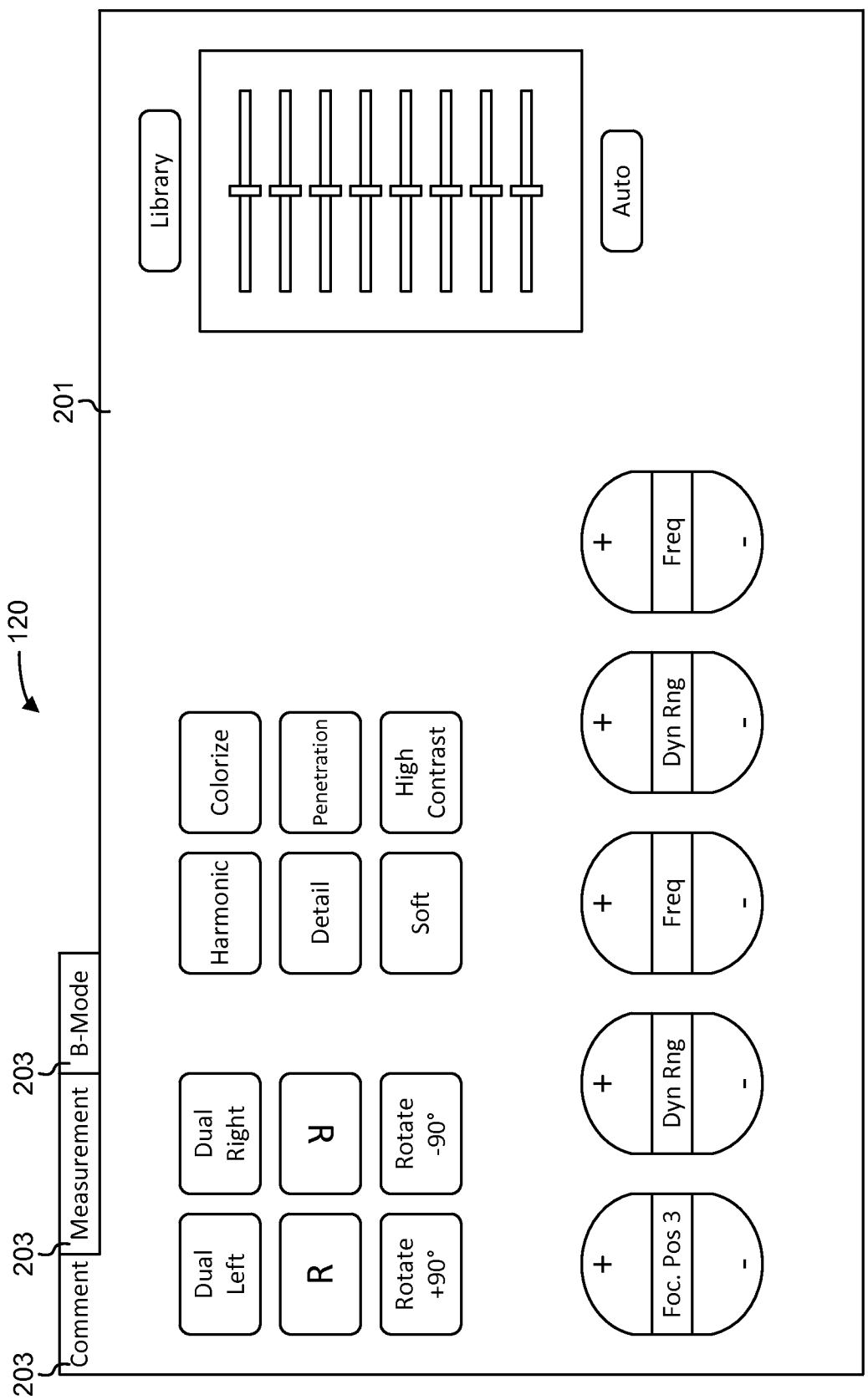
FIG. 13B illustrates a user interface corresponding to the activation of a function.

FIG. 13B illustrates an embodiment of touchscreen 120 and touchscreen UI 201 which corresponds to the instance of the function stack 501 depicted in FIG. 13A. The function which owns touchscreen 120 as an input device (e.g., the currently selected function tab 203) is signified by the corresponding tab 203 forming a part of the screen containing available settings, buttons, fields, information, etc. For example, comment tab 203 corresponds to comment function 507 owning touchscreen 120. Functions which are not currently selected (e.g., do not occupy the highest position 515 of function stack 501) but are active (e.g., the functions which may receive inputs from input devices other than the ones owned by the selected function) are signified by the corresponding tab 203 being displayed as a selectable choice but not an integral part of the screen containing input widgets or controls. For example, measurement function 505 and B-mode function 503 are active functions as signified by corresponding tabs 203 and are part of function stack 501. Each active function claims touchscreen 120 as a resource, but only the selected function owns the resource so as to receive inputs from the controls or widgets. Input devices and/or resources which are not owned by a function may be owned by other functions according to their priority assigned by processing circuit 163.

Figure 13C:
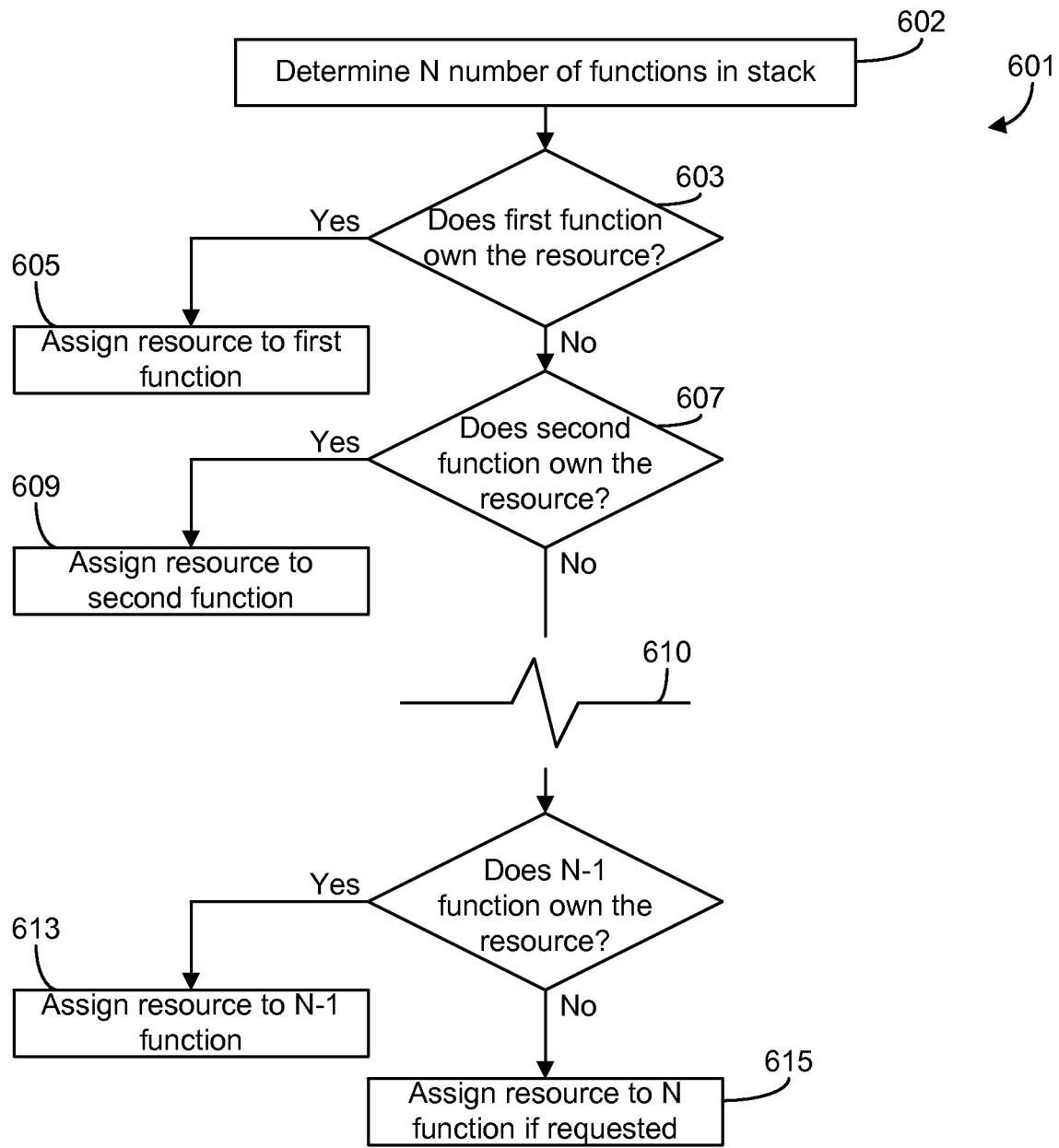
FIG. 13C illustrates a flow chart of the programming logic used to assign resources to functions according to one embodiment.

With reference to FIGS. 13A and 13C, FIG. 13C illustrates a flow chart 601 of the programming logic used by processing circuit 163 and function stack 501 to assign resources according to one embodiment. First, the number of active functions in function stack 501 is determined (602). For example, the number of functions in function stack 501 may be N=1 as depicted in FIG. 13A. It is then determined if the first function (e.g., the function in highest position 515) owns the requested resource (603). The function in highest potion 515 owns all requested resources. If the resource is requested it is owned by the function in the highest position 515 of function stack 501. For example, if comment function 507 requests touchscreen 120 it owns touchscreen 120 because it occupies highest position 515. Processing circuit 163 assigns the owned resource to the first function if the first function owns the resource (605). The first function may then receive inputs, generate outputs, or use computational resources of the assigned resource. For example, comment function 507 is assigned touchscreen 120 and may receive user inputs through presses on touchscreen 120 and display outputs on touchscreen 120.

If the first function does not own the resource, processing circuit 163 determines if the function in second position 517 owns the resource (607). If the requested resource is not owned by the first function and is requested by the function in second position 517, then the function in second position 517 owns the requested resource. If it is determined that the requested resource is owned by the function in second position 517, processing circuit 163 assigns the resource to the function in second position 517 (609). The function in second position 517 may then receive inputs, generate outputs, or use computational resources of the assigned resource. For example, measurement function 505 requests keyboard 281 which is not owned by the first function. Processing circuit 163 assigns keyboard 281 to measurement function 505, and measurement function 505 may receive user inputs through keyboard 281. If the requested resource is not owned by the first function and is not requested by the function in the second position 517 then the resource remains available to functions lower in function stack 501.

As illustrated by break 610, the above described sequence of steps repeats for functions in other positions within function stack 501. Processing circuit 163 determines if the penultimate function (e.g., the second lowest function in function stack 501, N−1 function) owns the requested resource (613). If the resource is owned by the penultimate function (e.g., the penultimate function requests an unassigned resource), then processing circuit 163 assigns the resource to the penultimate function (613). If the penultimate function does not own the requested resource, it is assigned to the last function (e.g., function on bottom of function stack 501, N function) if the last function requests the resource (615). If the last function does not request the resource and no previous function has requested the resource, the resource remains unassigned. An unassigned resource does not provide input to any function and does not receive output from any function. The sequence illustrated by flow chart 600 may be iterative for each resource of portable ultrasound system 100.

In some embodiments, the programming logic of flow chart 600 or a portion thereof is repeated during operation of portable ultrasound system 100. The process of assigning resources may be repeated each time a resource is requested by a function. In other embodiments, the process or a portion of the process is repeated upon the occurrence of an event. For example, the process or portion of the process may repeat when a function is activated. In one embodiment, the process or portion of the process may repeat when a function is selected.

Figure 14A:
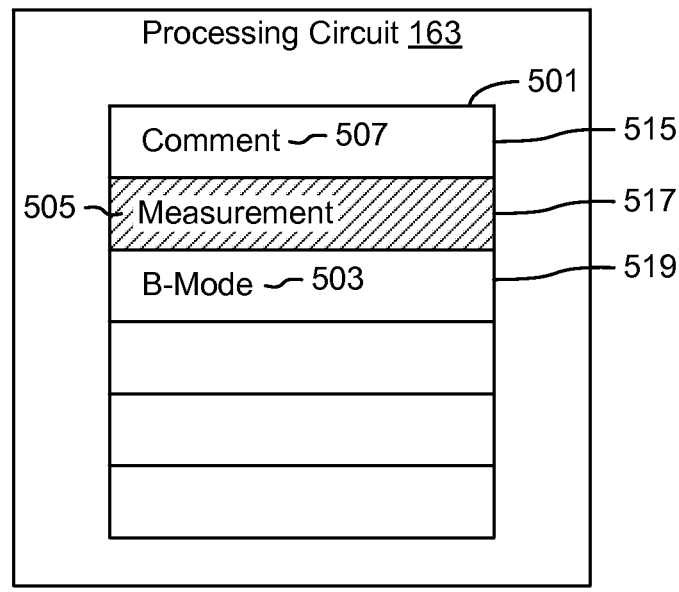
FIG. 14A illustrates a function in the function stack which is being exited by a user according to an exemplary embodiment
Figure 14B:
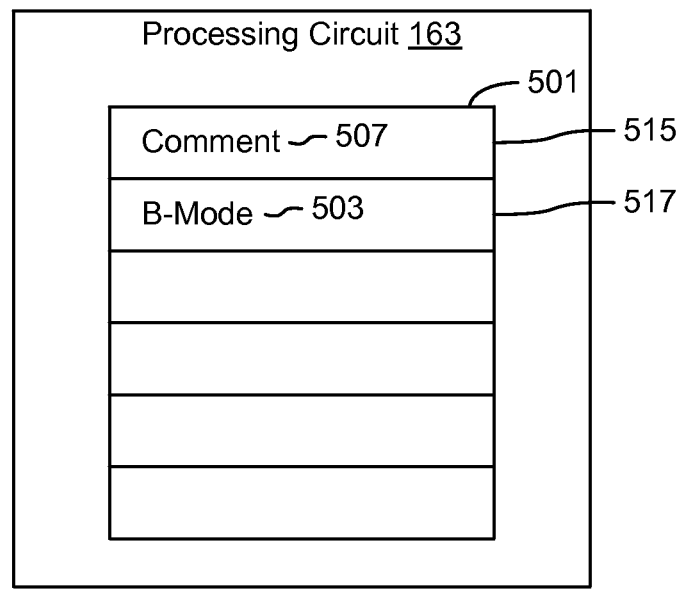
FIG. 14B illustrates a function stack following the exiting of a function according to an exemplary embodiment.

With reference to FIGS. 13B and 14A-14C, when a user exits a function, the function is no longer active. The exited function is then removed from function stack 501. A user may exit a function by closing the function (e.g., pushing a button which closes the function). In some embodiments, a user may be prompted by portable ultrasound system 100 through touchscreen UI 201, touchpad or touchscreen 110, and/or main screen 130 to close functions which have not been recently used. Closing or exiting functions may free up resources (e.g., computational resources, input devices, output devices, etc.) for the remaining active functions. As illustrated in FIG. 14A according to one embodiment, measurement function 505 has been exited by a user. This is illustrated by the shading. Measurement function 505 is removed from the second position 517 of function stack 501. This results in the function stack 501 as illustrated by FIG. 14B. Comment function 507 remains in the highest position 515, and B-mode function 503 is moved from the previous location of the third position 519 to the second position 517. The resources owned by measurement function 505 are unassigned by processing circuit 163. Unassigned resources are available to other functions. For example, B-mode function 503 may now own resources previously owned by measurement function 505.

Figure 14C:
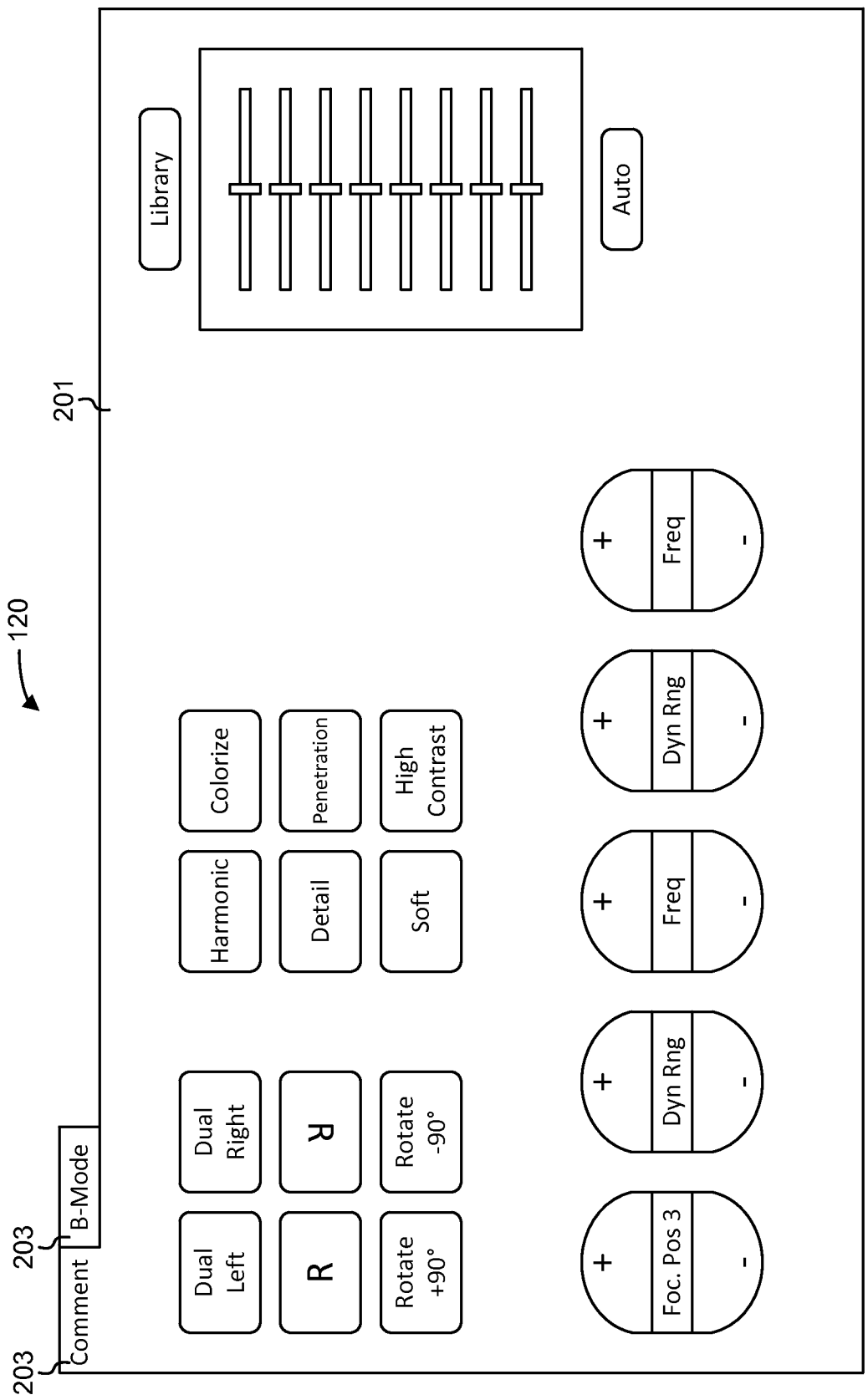
FIG. 14C illustrates an embodiment of a user interface showing the results of exiting a function.

Touchscreen UI 201 and/or other resources are updated (e.g., by processing circuit 163) to reflect the exiting of a function 505. For example, touchscreen UI 201 as depicted in FIG. 13B before measurement function 505 is exited shows measurement function 505 with an associated tab 203. After measurement function 505 is exited touchscreen UI 201 is updated as illustrated in FIG. 14C. Measurement function 505 and the associated tab 203 are removed from the display on touchscreen 120. Tabs 203 are also reorganized to account for the removal of measurement function 505. Comment function 507 and B-mode function 503 are displayed with their respective tabs 203.

Functions may also be switched between. A new function may be selected from all active functions. In some embodiments, the selected function is switched by portable ultrasound system 100 in response to an event. For example, if an ultrasound probe is connected to portable ultrasound system, main circuit board 161 may detect that is has been attached and select an imaging function such as B-mode using processing circuit 163 and function stack 501. In some embodiments, a user may switch between functions by selecting a function using its corresponding tab 203 within touchscreen UI 201.

Figure 15A:
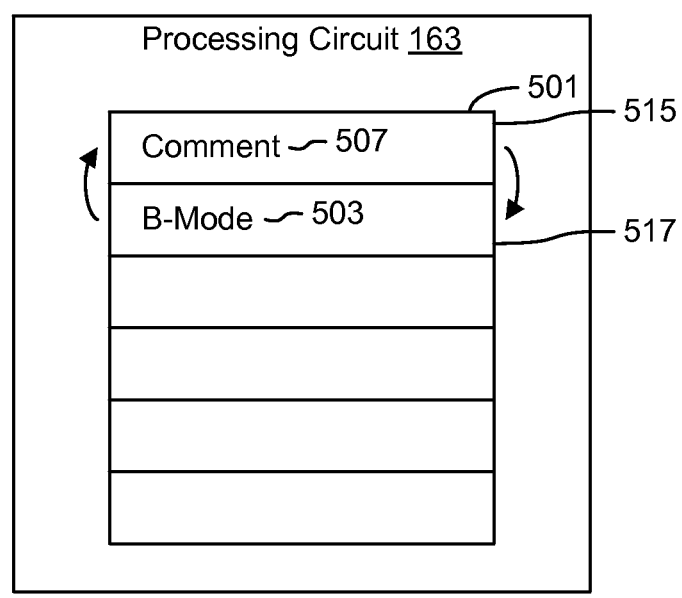
FIG. 15A illustrates an embodiment of a function stack in response to selecting a new function in the user interface.

FIG. 15A illustrates a function being selected. A selected function is moved to the top of function stack 501 and occupies the highest position 515 of function stack 501. In some embodiments, the previously selected function is moved to second position 517 with all other active functions above the position previously occupied by the newly selected function shifting down one position. The function below the position previously occupied by the newly selected function moves up one position to occupy the position of the previously selected function. The remaining functions are moved up one position. In other embodiments, the newly selected function is moved to the highest position 515 of function stack 501 and the previously selected function takes the position vacated by the newly selected function. In further embodiments, the newly selected function is moved to the highest position 515 of function stack 501 and the active functions move up to occupy any vacated positions. The previously selected function is then moved to the lowest unoccupied position.

For example, comment function 507 may be the selected function. A user then selects the other active function B-mode function 503. B-mode function 503 is moved to occupy the highest position 515 of function stack 501. Comment function 507 remains active but is moved to the second position 517 of function stack 501.

Figure 15B:
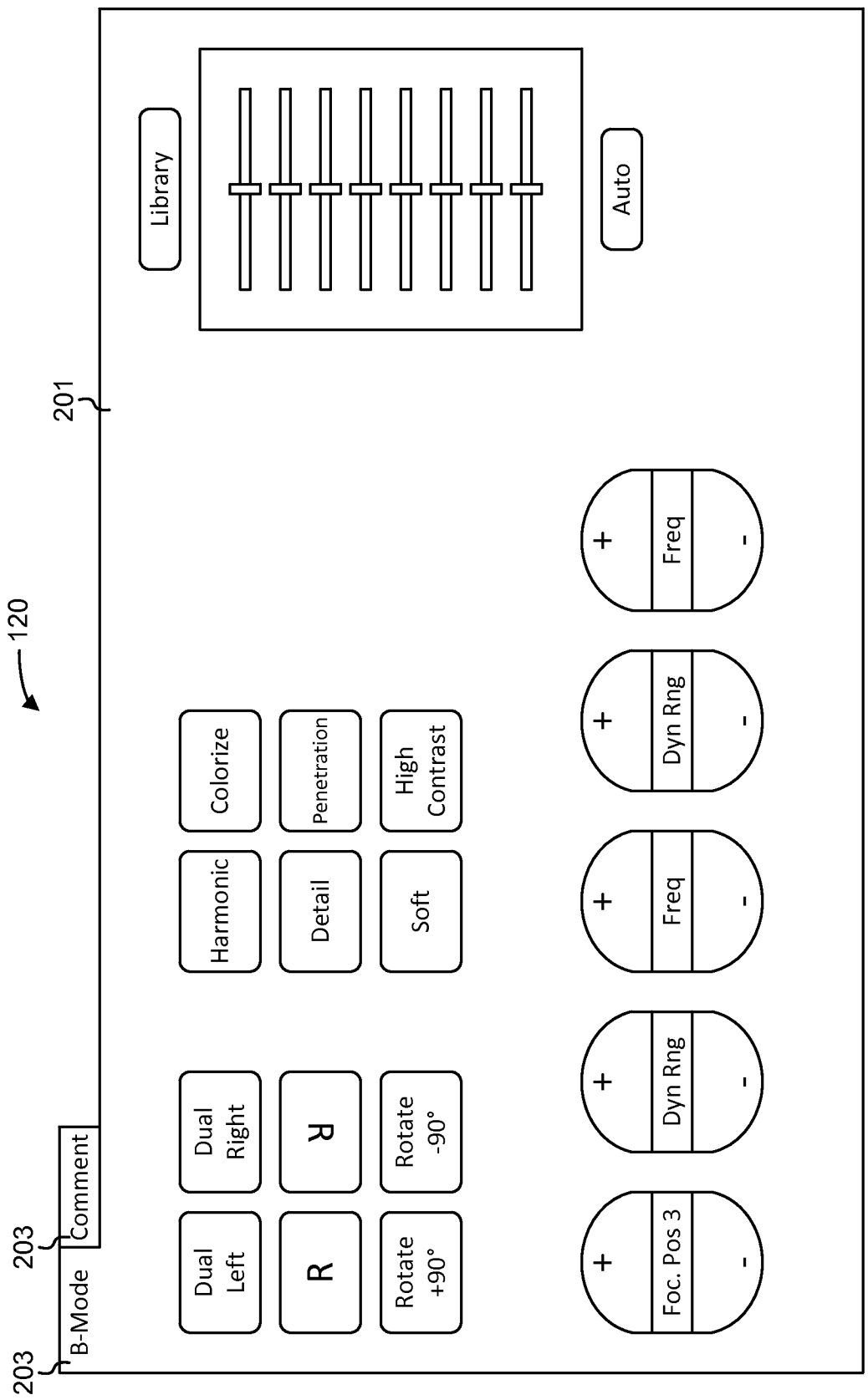
FIG. 15B illustrates an embodiment of a user interface in response to selecting a new function.

Touchscreen UI 201 and/or other resources are updated (e.g., by processing circuit 163) to reflect the selecting of a function. The order of tabs 203 of touchscreen UI 201 may be updated to reflect the selected function. Continuing the example, FIG. 14C illustrates touchscreen UI 201 with comment function 507 selected. Following the selection of B-mode function 503 by a user, touchscreen UI 201 is updated. FIG. 15B reflects the updated touchscreen UI 201 to account for the user selection of B-mode function 503. The tab 203 corresponding to B-mode function 503 is moved furthest to the left and forms an integral part of the screen with the widgets. The tab 203 associated with comment function 507 is moved to the right and sectioned from the screen.

Figure 16:
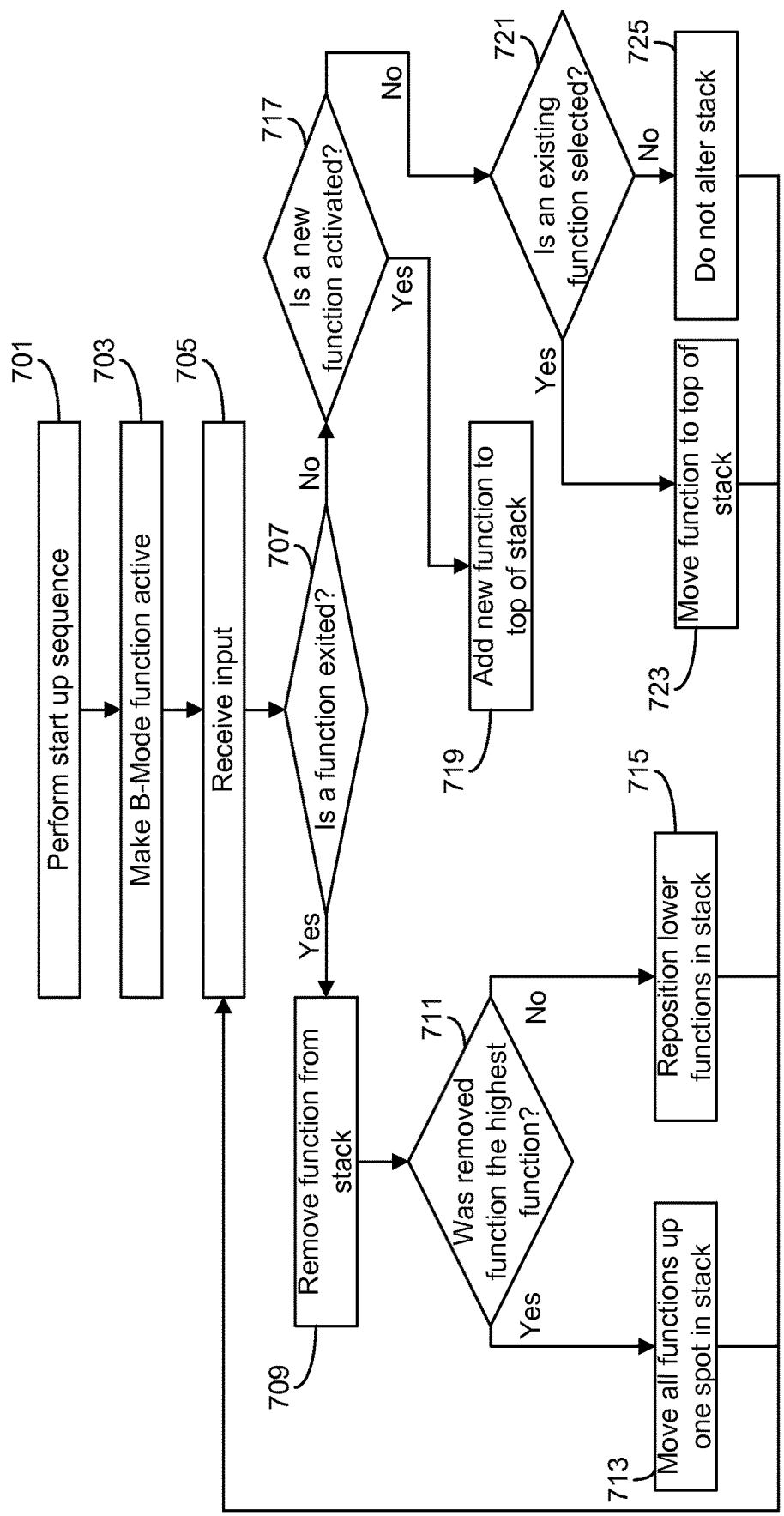
FIG. 16 illustrates a flow chart of the programming logic used to assign positions to functions within a function stack according to an exemplary embodiment.

FIG. 16 illustrates a flow chart 700 of the programming logic used by processing circuit 163 and function stack 501 to assign positions to functions within function stack 501 according to one embodiment. Portable ultrasound system 100 performs a startup sequence (701). For example, processing circuit 163 may prepare portable ultrasound system 100 for use by user. Following startup, B-mode function 503 is activated by processing circuit 163 and is selected (703). B-mode function 503 is moved to the highest position 515 of function stack 501. In other embodiments, different functions may be activated following startup as the first function. For example, A-mode may be the function activated following startup. In some embodiments, a user may determine which function is activated following startup by selecting a preference through the user interface of portable ultrasound system 100. In further embodiments, no function is activated following startup. Functions are only activated by user input.

Processing circuit 163 receives an input (705). The input received may be one of a function exit command, user key press input, system event, etc. In some embodiments, the input may be received by processing circuit 163 from main circuit board 161. Main circuit board 161 may in turn have received the input through a device connected to main circuit board 161. For example, the device may be a user input device such as keyboard 281 connected to main circuit board 161 through user input interface 173. The input (e.g., a command instruction or an input which generates a command instruction) may then be executed by processing circuit 163. It is then determined if a function has been exited as a result of the input (707).

If a function has been exited, the function is removed from function stack 501 (709). It is determined if the removed function was in the highest position 515 of function stack 501 (713). If the removed function was in the highest position 515 of function stack 501, all remaining active functions are moved up one spot (713). The function then in the highest position 515 of function stack 501 is made the selected function. If the removed function was not in the highest position 515 of function stack 501, the remaining active functions which were lower than the removed function are repositioned (715). For example, all remaining active functions lower than the removed function may be moved up one position within function stack 501 such that the empty space is occupied.

If a function has not been exited following the input, it is determined if a new function has been activated (717). If a new function has been activated (e.g., a previously inactive function is made active), the new function is moved to the highest position 515 of function stack 501 (719). The existing active functions are all shifted down function stack 501 by one position. If a new function has not been activated, it is determined if an existing active function has been selected (721). If an existing active function has been selected, the newly selected function is moved to the highest position 515 of function stack 501 (723). The other active functions are repositioned within function stack 501. The repositioning may be any of the techniques previously described with respect to selecting functions and FIG. 15A. If an existing active function is not selected, then function stack 501 is not altered (725). The process described above may be repeated upon each start-up of portable ultrasound system 100. The process may also repeat itself stating at receiving an input (705) when an input is received. In some embodiments, processing circuit 163 may perform the actions described above. For example, processing circuit 163 may receive inputs, reorder function stack 501, remove function from function stack 501, etc. In some embodiments, processing circuit 163 may make the determination described above. For example, processing circuit 163 may determine if a function is exited, if a new function is activated, if a function is selected, etc.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A portable ultrasound system, comprising:
  a main screen included in a hinged portion of the portable ultrasound system configured to open and close relative to a main housing of the portable ultrasound system;
  a touchscreen included on a top surface of the main housing of the portable ultrasound system;
  a touchpad included on the top surface of the main housing of the portable ultrasound system; and
  a processing circuit configured to perform general computing operations and configured to receive ultrasound imaging data,
  wherein the processing circuit is further configured to provide ultrasound information to at least one of the main screen, the touchscreen, or the touchpad, and
  wherein the processing circuit is further configured to receive a touch input from at least one of the touchpad or the touchscreen while operating in a pulsed wave Doppler (PW) function mode and display an ultrasound imaging user interface on the at least one of the touchpad or the touchscreen including a plurality of control options or settings for use in ultrasound imaging, the ultrasound imaging interface including a gate icon corresponding to a blood flow analysis gate for a Doppler gate used for measuring blood flow during operation in the PW function mode, the touch input including a gesture performed on the at least one of the touchpad or the touchscreen, the processing circuit configured to adjust an alignment of the blood flow analysis gate based on the gesture, the processing circuit configured to determine if the touch input includes instructions to rotate the gate icon, determine if the touch input includes instructions to modify a size of the gate icon, and determine if the touch input includes instructions to modify a position of the gate icon, the processing circuit configured to update the display of the blood flow analysis gate of the ultrasound imaging user interface on the at least one of the touchpad or the touchscreen by rotating the gate icon if the touch input includes instructions to rotate the gate icon, modify the size of the gate icon if the touch input includes instructions to modify the size of the gate icon, and modify the position of the gate icon if the touch input includes instructions to modify the position of the gate icon, the processing circuit configured to determine a mode of operation, receive a swipe input in a swipe region of the touchpad, perform gain control responsive to receiving the swipe input in the swipe region while the mode of operation is a B-mode, and perform frame-by-frame review responsive to receiving the swipe input in the swipe region while the mode of operation is a freeze mode by advancing displayed images by a frame responsive to the swipe input.

2. The portable ultrasound system of claim 1, wherein the processing circuit is configured to display an ultrasound image on the main screen.

3. The portable ultrasound system of claim 1, wherein the processing circuit is configured to display an ultrasound imaging user interface on the touchscreen including a plurality of control options or settings for use in ultrasound imaging, and wherein the processing circuit is further configured to receive touch input from the touchscreen and adjust the ultrasound imaging based on the received touch input.

4. The portable ultrasound system of claim 1, wherein the processing circuit is configured to receive touch input from the touchpad, and wherein the processing circuit is further configured to at least one of adjust a displayed ultrasound image on the main screen, adjust a displayed user interface on the touchscreen, or adjust the ultrasound imaging based on the received touch input.

5. The portable ultrasound system of claim 1, wherein the touchpad is located below the touchscreen on the top surface of the main housing relative to the touchscreen.

6. The portable ultrasound system of claim 1, further comprising a keyboard included on the top surface of the main housing and including a plurality of buttons configured to provide input to the processing circuit.

7. The portable ultrasound system of claim 1, wherein the processing circuit is configured to receive the ultrasound imaging data from a removable ultrasound module.

8. A portable ultrasound system, comprising:
a main screen included in a hinged portion of the portable ultrasound system configured to open and close relative to a main housing of the portable ultrasound system;
a touchscreen included on a top surface of the main housing of the portable ultrasound system; and
a processing circuit configured to:
perform general computing operations and configured to receive ultrasound imaging data,
provide ultrasound information to at least one of the main screen or the touchscreen,
display, while operating in a pulsed wave Doppler (PW) function mode, an ultrasound imaging user interface on the touchscreen including a plurality of control options or settings for use in ultrasound imaging, the ultrasound imaging interface including a gate icon corresponding to a blood flow analysis gate for a Doppler gate used for measuring blood flow during operation in the PW function mode,
receive a swipe input in a swipe region of the touchpad;
responsive to receiving the swipe input and determining a mode of operation to be a B-mode, perform gain control based on the swipe input in the swipe region; and
responsive to receiving the swipe input and determining the mode of operation to be a freeze mode, perform frame-by-frame review based on the swipe input in the swipe region by advancing displayed images by a frame responsive to the swipe input.

9. The portable ultrasound system of claim 8, wherein the ultrasound imaging interface comprises a distance gain compensation widget including a plurality of sliders configured to allow for adjustment of gain at various positions of an imaged area displayed on the main screen, and wherein the distance gain compensation widget is configures to adjust multiple sliders of the plurality of sliders in response to a single swipe style user input crossing the multiple sliders vertically.

10. The portable ultrasound system of claim 9, wherein the distance gain compensation widget is configured to adjust the multiple sliders by moving a set value of the slider towards the direction of single swipe style user input crossing the multiple sliders vertically in response to receiving the input.

11. The portable ultrasound system of claim 8, wherein the ultrasound imaging interface comprises a library button configured to store a plurality of different buttons which a user can drag and drop into empty space of the ultrasound imaging interface to add to a customized set of interface elements included in the ultrasound imaging interface.

12. The portable ultrasound system of claim 8, wherein the ultrasound imaging interface comprises a plurality of tabs, each tab corresponding to a different ultrasound imaging function and each tab including a plurality of user input features.

13. The portable ultrasound system of claim 8, further comprising a keyboard included on the top surface of the main housing and including a plurality of buttons configured to provide input to the processing circuit.

14. The portable ultrasound system of claim 8, further comprising a touchpad included on the top surface of the main housing of the portable ultrasound system, wherein the processing circuit is configured to receive touch input from the touchpad, and wherein the processing circuit is further configured to at least one of adjust a displayed ultrasound image on the main screen, adjust the displayed user interface on the touchscreen, or adjust ultrasound imaging based on the received touch input.

15. The portable ultrasound system of claim 8, wherein the processing circuit is configured to display only the ultrasound imaging user interface on the touchscreen, and wherein an ultrasound image is not displayed on the touchscreen.

16. A portable ultrasound system, comprising:
a main screen included in a hinged portion of the portable ultrasound system configured to open and close relative to a main housing of the portable ultrasound system;

a touchpad included on the top surface of the main housing of the portable ultrasound system and configured to receive touch based inputs and display images, the touchpad defining a plurality of defined regions, the touchpad configured to receive a gesture input via each of the plurality of defined regions; and a processing circuit configured to perform general computing operations and configured to receive ultrasound imaging data, wherein the processing circuit is further configured to provide ultrasound information to at least one of the main screen or the touchpad, and wherein the processing circuit is further configured to control the display of the images on the touchpad to cause the touchpad to display an input image on each defined region identifying a type of gesture input in the each defined region, receive input from the touchpad corresponding to the gesture input, wherein the type of gesture input received in a subset of the plurality of defined regions is controlled by the processing circuit based on a selected mode of operation of a plurality of modes of operation of the portable ultrasound system, wherein the plurality of modes of operation include at least a B-mode and a freeze mode, wherein in the B-mode, the processing circuit performs gain control based on a swipe input in a swipe region of the touchpad, and in the freeze mode, the processing circuit performs frame-by-frame review based on the same swipe input by advancing displayed images responsive to the swipe input.

17. The portable ultrasound system of claim 16, wherein the processing circuit is configured to receive gesture based input from the touchpad, and wherein the processing circuit is further configured to display images on the touchpad which illustrate to a user how to perform a gesture based input.

18. The portable ultrasound system of claim 17, wherein the processing circuit displays images which illustrate to the user how to perform the gesture based input by displaying an animation illustrating the gesture and a resulting response to the gesture based input.

19. The portable ultrasound system of claim 16, wherein the processing circuit is configured to cause the touchpad to display an illustration of a gesture in response to at least one of an imaging mode change, a function selection, or a widget press.

* * * * *